US007740795B2

(12) United States Patent
Wang et al.

(10) Patent No.: US 7,740,795 B2
(45) Date of Patent: Jun. 22, 2010

(54) POROUS METALLIC SCAFFOLD FOR TISSUE INGROWTH

(75) Inventors: Kathy K. Wang, Suffern, NY (US); Nicholas Nai Guang Dong, Little Falls, NJ (US); Michael Meehan, Wanaque, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 411 days.

(21) Appl. No.: 11/179,385

(22) Filed: Jul. 12, 2005

(65) Prior Publication Data
US 2006/0003179 A1 Jan. 5, 2006

Related U.S. Application Data

(62) Division of application No. 10/071,667, filed on Feb. 8, 2002, now Pat. No. 7,458,991.

(51) Int. Cl.
*B22F 3/11* (2006.01)
(52) U.S. Cl. .............................. 419/2; 419/23; 419/26; 419/36; 623/23.55; 428/613; 75/415; 427/2.26
(58) Field of Classification Search .................. 419/20, 419/2
See application file for complete search history.

(56) References Cited

U.S. PATENT DOCUMENTS

| | | |
|---|---|---|
| 2,694,647 A | 11/1954 | Cole |
| 3,502,493 A | 3/1970 | Forestek |
| 3,694,325 A | 9/1972 | Katz et al. |
| 3,695,869 A | 10/1972 | Hivert et al. |
| 3,711,279 A | 1/1973 | Hivert et al. |
| 3,753,757 A | 8/1973 | Rodgers et al. |

(Continued)

FOREIGN PATENT DOCUMENTS

EP 0 075 438 A1 3/1983

(Continued)

OTHER PUBLICATIONS

John Banhart, "Manufacture, characterization and application of cellular metals and metal foams," Progress in Materials Science 46 (2001) 559-632.*

(Continued)

*Primary Examiner*—Roy King
*Assistant Examiner*—Christopher Kessler
(74) *Attorney, Agent, or Firm*—Lerner, David, Littenberg, Krumholz & Mentlik, LLP

(57) ABSTRACT

The invention relates to implantable medical devices, particularly, to porous structures for such devices. In one aspect, the invention provides a porous metal scaffold comprising a porous metal network having pores defined by metal webs, the metal webs covered with at least one layer of metal particles bonded to the metal webs. In other aspects, the invention provides methods of forming porous scaffolds. In one such aspect, the method includes providing a polymer foam; forming a skin of biocompatible metal on the polymer foam by low temperature arc vapor deposition; and heating the polymer foam and the metal skin above the decomposition temperature of the polymer foam in an inert gas atmosphere; thereby the polymer foam decomposes producing a green metal foam. In yet other aspects, the invention provides methods of improving stability of porous scaffolds.

26 Claims, 18 Drawing Sheets

U.S. PATENT DOCUMENTS

| | | | |
|---|---|---|---|
| 3,852,045 A | 12/1974 | Wheeler et al. | |
| 3,897,221 A | 7/1975 | Sayler et al. | |
| 4,064,567 A | 12/1977 | Burstein et al. | |
| 4,076,888 A | 2/1978 | Perugini et al. | |
| 4,156,943 A | 6/1979 | Collier | |
| 4,351,855 A | 9/1982 | Pinkhasov | |
| 4,542,539 A | 9/1985 | Rowe et al. | |
| 4,562,039 A | 12/1985 | Koehler | |
| 4,569,821 A | 2/1986 | Duperray et al. | |
| 4,612,160 A | 9/1986 | Donlevy et al. | |
| 4,613,369 A | 9/1986 | Koehler | |
| 4,775,598 A | 10/1988 | Jaeckel | |
| 4,822,692 A | 4/1989 | Koehler | |
| 4,855,101 A | 8/1989 | Mohs et al. | |
| 4,871,621 A | 10/1989 | Bagley et al. | |
| 4,888,114 A | 12/1989 | Gaddis et al. | |
| 4,957,543 A | 9/1990 | Babjak et al. | |
| 4,975,230 A | 12/1990 | Pinkhasov | |
| 5,011,638 A | 4/1991 | Pinkhasov | |
| 5,018,285 A | 5/1991 | Zolman et al. | |
| 5,034,186 A | 7/1991 | Shimamune et al. | |
| 5,104,410 A | 4/1992 | Chowdhary | |
| 5,141,581 A | 8/1992 | Markham | |
| 5,178,908 A | 1/1993 | Koyama | |
| 5,282,861 A | 2/1994 | Kaplan | |
| 5,336,465 A | 8/1994 | Matsunaga et al. | |
| 5,364,586 A | 11/1994 | Trusov et al. | |
| 5,374,491 A | 12/1994 | Brannan et al. | |
| 5,417,917 A | 5/1995 | Takahar et al. | |
| 5,441,919 A | 8/1995 | Park et al. | |
| 5,443,510 A | 8/1995 | Shetty et al. | |
| 5,640,669 A | 6/1997 | Harada et al. | |
| 5,734,959 A | 3/1998 | Krebs et al. | |
| 5,735,977 A | 4/1998 | Cushnie et al. | |
| 5,747,110 A | 5/1998 | Tallentire et al. | |
| 5,749,041 A | 5/1998 | Lakshminarayan et al. | |
| 5,839,049 A | 11/1998 | Ettel et al. | |
| 5,848,351 A | 12/1998 | Hoshino et al. | |
| 5,879,743 A | 3/1999 | Revankar | |
| 5,881,353 A | 3/1999 | Kamigata et al. | |
| 5,897,592 A | 4/1999 | Caldarise et al. | |
| 5,926,685 A | 7/1999 | Krebs et al. | |
| 5,976,454 A | 11/1999 | Sterzel et al. | |
| 6,008,432 A | 12/1999 | Taylor | |
| 6,033,788 A | 3/2000 | Cawley et al. | |
| 6,066,176 A * | 5/2000 | Oshida | 623/23.62 |
| 6,087,553 A | 7/2000 | Cohen et al. | |
| 6,106,890 A | 8/2000 | Hayashi | |
| 6,132,674 A | 10/2000 | Compton et al. | |
| 6,171,532 B1 | 1/2001 | Sterzel | |

FOREIGN PATENT DOCUMENTS

| | | |
|---|---|---|
| EP | 98518 | 1/1984 |
| EP | 0 801 152 A1 | 10/1997 |
| EP | 1 052 321 A1 | 11/2000 |
| GB | 624 175 A1 | 5/1949 |
| JP | 10 046268 A1 | 2/1998 |
| WO | WO-83/00282 | 2/1983 |
| WO | WO-01/72664 A1 | 10/2001 |
| WO | WO-02/17820 A1 | 3/2002 |
| WO | WO-02/059396 A1 | 8/2002 |
| WO | WO-02/066693 A1 | 8/2002 |

OTHER PUBLICATIONS

Queheillalt et al, Synthesis of oepn-cell metal foams by templated directed vapor deposition, Journal of Materials Research, vol. 16, No. 4, Apr. 2001, pp. 1028-1036.

* cited by examiner

PRIOR ART

POROUS METALLIC SCAFFOLD FOR TISSUE INGROWTH

CROSS-REFERENCE TO RELATED APPLICATIONS

This application is a divisional of U.S. application Ser. No. 10/071,667, now U.S. Pat. No. 7,458,991, filed on Feb. 8, 2002, the disclosure of which is incorporated herein by reference.

FIELD OF THE INVENTION

The present invention relates to implantable medical devices, and in particular to porous scaffolds for implantable medical devices, especially orthopedic implants, methods of forming such scaffolds, and methods of producing such devices.

BACKGROUND OF THE INVENTION

The use of orthopedic implants is the result of deterioration of human bone structure, usually because of various degenerative diseases, such as osteoarthritis. In recent years, a variety of implantable orthopedic devices had been developed. Typically, the failed bone structure is replaced with an orthopedic implant that mimics the structure of the natural bone and performs its functions.

Orthopedic implants are constructed from materials that are stable in biological environments and withstand physical stress with minimal deformation. Such materials must possess strength, resistance to corrosion, biocompatibility, and good wear properties. Also, the implants include various interacting parts, which undergo repeated long-term physical stress inside the body.

A breakdown of a permanently installed implant leads to pain, limitation on the range of motion, and may require a replacement of the implant. For these reasons, among others, the bone/implant interface and the connection between various parts of the implant must be resistant to breakdown. It is especially important since installation of an orthopedic implant often involves extensive and difficult medical procedure, and therefore replacement of the installed implant is highly undesirable.

The requirements for the useful life of the implant continue to grow with the increase in the life expectancy. The strength and longevity of implants in large part depend on the bone/implant interface. Various methods of connection are known in the art. For example, a hip joint is a ball-in-socket joint, and includes a rounded femoral head and a cup-like socket (acetabular cup) located in the pelvis. The surfaces of the rounded femoral head and the acetabular cup continually abrade each other as a person walks. The abrasion creates stress on the bones that bear the acetabular cup and the femoral head. If the femoral head or the acetabular cup is replaced with an implant, this stress must be well tolerated by the implant's bearing surfaces to prevent implant failure.

FIG. 1 shows a typical hip replacement system that includes an acetabular cup prosthetic assembly 10 and a femoral prosthesis 20. Generally, the acetabular cup implant 10 includes a bone interface shell 11 and a socket bearing insert 12. The femoral prosthesis 20 includes a femoral stem 21 and a femoral head in the form of a ball 22, which moves inside the socket insert 12 of the acetabular cup implant 10. The femoral ball 22 usually has a polished surface to maintain a LOW friction interface with the surface of the socket insert 12 of the acetabular cup 10. The stem section 21 is inserted into the interior of the femur and may have a bone interface surface 26.

The socket insert 12 is usually made from a plastic material such as polyethylene or ultra high molecular weight polyethylene (UHMWPE), but may be of any biocompatible material that has sufficient strength and wear resistance to withstand the pressures and abrasive nature of the joint. The socket insert 12 is typically held in the shell 11 by a series of locking grooves or notches. In turn, the complete acetabular cup implant 10 may be attached to the patient's pelvis by a series of locking grooves, pins or screws 29. Alternatively, the acetabular cup implant 10 may be press-fit by being driven into the patient's acetabulum with a proper impaction tool without the fixing pins in situations where patient-related criteria are met. This method avoids the use of bone cement. The shell 11 is typically made from a metal such as titanium or cobalt-chrome alloy, and has a bone interface surface 16.

In use, the bone interface surfaces 16 and 26 must bear a significant lateral and axial stress. The increased requirements for useful life of the implant make it especially important that these surfaces tolerate such stress. The prior art takes several approaches to this problem.

Thus, the entire acetabular cup implant 10, including both the shell 11 and the socket insert 12, may be cemented to the acetabulum or the cup may be produced as a single piece from ultra high molecular weight polyethylene and anchored into the acetabulum with bone cement. Another way to improve the longevity of orthopedic implants is to provide a porous bone interface surface to receive ingrowth of bone tissue thereby binding the natural bone to the implant. The bone ingrowth into the voids of the porous bone interface layer provides skeletal fixation for the implants used for replacement of bone segments. In addition to lateral and axial strength enhancement, the bone ingrowth improves biocompatibility of the implant and is even believed by some to promote positive biochemical changes in the diseased bone. To implement this approach, it is important to develop methods of constructing porous outer layers on the bone interface surfaces of implants.

Orthopedic implants with porous bone interface surfaces have been studied extensively over the last twenty years. It has long been known that the success in facilitating the ingrowth is related to the pore characteristics of the bone interface surfaces, such as pore size and pore volume. For example, it is known that the bone ingrowth may be almost entirely non-existent if the porous layer has pore sizes of less than 10 µm, and that pore sizes greater that 100 µm facilitate the ingrowth.

In view of the strength and longevity requirements, the implants are typically made of biocompatible metals, such as titanium or cobalt-chrome alloy. Thus, one of the challenges is to provide metallic orthopedic implants having porous metallic bone interfaces with high porosity. Another challenge is to provide an integrated bond between the porous layer and the underlying solid substrate, such as the surface 16 and the bulk of the shell 11, respectively, of the acetabular cup implant 10 shown in FIG. 1.

Certain orthopedic implants having porous bone interface surfaces, and related methods of making such implants have been patented. U.S. Pat. No. 5,282,861 describes an open cell tantalum structures for bone implants having pore volume of from 70 to 80%. The open cell tantalum structures of the '861 patent are formed by chemical vapor deposition of tantalum on a carbon skeleton. The resulting structures have a carbon core and a tantalum outer surface.

U.S. Pat. No. 6,087,553 describes tantalum/polyethylene composites suitable for use in orthopedic implants. The composites have a pore volume of 50 to 90%. The implants produced from the composites of the '553 patent are not modular and not metal-backed.

In general, methods of producing high pore volume metals are known in the art. U.S. Pat. No. 5,976,454 describes a process for producing nickel foam for use in making battery electrodes. The porosity of the foam is over 90%, but it is produced by a method that is in many respects not suitable for producing foams of biocompatible metals typically used in making implants, such as tantalum or titanium.

U.S. Pat. No. 5,926,685 describes a method of forming an implant having a porous outer surface by using an organic binder compound to enhance the binding between the porous surface layer and the implant. The binder and metal particles that would form the porous layer are mixed and the mixture is placed in contact with a solid surface of the metallic implant. Then, the particles (pre-cursor of the porous layer) are bound to each other and to the solid surface of the implant via a sintering process. The '685 patent does not describe production of a metal foam as a pre-cursor to the porous layer. Also, the '685 patent does not describe the porosity of the porous layer.

Therefore, there exists a continuing need for implantable medical devices, especially orthopedic implants, having porous surfaces, blocks, layers or other porous structures for interfacing with bones and/or other tissue, with the porous structures having a variety of desirable characteristics, including high porosity, uniform pore size, and high strength.

SUMMARY OF THE INVENTION

Various aspects of the present invention address this need. Thus, in accordance with one aspect, the invention provides a porous metal scaffold for use in an implantable medical device comprising a porous metal network having pores defined by metal webs, the metal webs covered with at least one layer of metal particles bonded to the metal webs. Preferably, the metal webs of the porous metal scaffold may form a continuous inner skeleton. The pore size of the porous scaffold may be varied by bonding additional layers of metal particles to the at least one layer of particles. Also, changing a size of the metal particles may also vary the pore size of the porous scaffold.

Preferably, the bonding between the metal webs and the metal particles is accomplished by sintering the metal particles to the webs. Also, preferably, the metal webs have partially hollow cores. The hollow cores of the metal webs may be surrounded by an outer web wall that has openings therein.

The pore size of the porous scaffold may range from 100 µm to 1000 µm. The pore volume may range from 50% to 90%. The scaffold may be formed into a shape having a thickness of 0.5 mm to 5 mm.

Preferably, the porous metal scaffold is bonded to a solid metal substrate. Also, preferably, the porous metal scaffold is directly bonded to the solid metal substrate. The metal scaffold may be sintered to the solid metal substrate. The scaffold may include a plurality of pores having a size greater than about 100 µm. The metal particles may have a size from 40 µm to about 80 µm. The metal of the particles is preferably selected from the group consisting of titanium, titanium alloy, cobalt chrome alloy, niobium and tantalum. The web metal is also preferably selected consisting of titanium, titanium alloy, cobalt chrome alloy, niobium and tantalum. The metal substrate may be part of an orthopedic implant.

In accordance with another aspect, the invention provides a method of forming a porous scaffold for use in an implantable medical device, the method including:

a) providing a polymer foam having a pre-determined thickness and a pore size ranging from about 500 µm to about 2000 µm;

b) forming a skin of biocompatible metal on the polymer foam by low temperature arc vapor deposition;

c) heating the polymer foam and the metal skin above the decomposition temperature of the polymer foam in an inert gas atmosphere; thereby the polymer foam decomposes producing a green metal foam.

Preferably, the method of this aspect of the invention further includes thickening the green metal foam by applying a solution of a binder onto the green foam, applying a metal powder having a pre-determined particle size, and sintering the foam, thus producing a final metal foam having a pre-determined pore size. The thickening of the foam may be repeated until the final metal foam has the pre-determined pore size.

Preferably, the pre-determined thickness of the polymer foam is between about 0.5 mm and about 10 mm, more preferably, between about 1 mm and about 5 mm, yet more preferably, between about 1 mm and about 2 mm. The preferred polymer foam is polyurethane foam. Preferably, the polymer foam has a pore size ranging from about 900 µm to about 1100 µm.

Preferably, the metal skin has thickness between about 1 µm and about 50 µm. More preferably, the polymer foam has a first side and a second side, and the thickness of the metal skin is about 35 µm on the first side and about 10 µm on the second side.

Preferably, the binder solution is an aqueous solution of methyl cellulose. Also, preferably, the pre-determined particle size of the metal particles used to thicken the metal web is between about 20 µm and about 100 µm, more preferably, between about 40 µm and about 80 µm.

Preferably, the pre-determined pore size of the final metal foam is between about 100 µm and about 1000 µm, more preferably, between about 300 µm and about 500 µm.

The invention also provides the green metal foam and the final metal foam produced by the method(s) of this aspect of the invention, as well as any intermediate metal foam. Preferably, the pre-determined pore size of the final metal foam produced by such method(s) is between about 100 µm and about 1000 µm, more preferably, between about 300 µm and about 500 µm, and/or a pore volume from about 50% to about 90%, more preferably, from about 60% to about 80%. The preferred final metal foam is made of titanium or titanium alloy.

The final metal foam produced by the method(s) of this aspect of the invention may be attached to a solid metal substrate. Such final metal foam may be included in the implantable medical device. The preferred implantable medical devices are orthopedic implants. One preferred device is an acetabular cup implant.

The biocompatible metal of the metal skin formed in the method of the invention may be titanium, titanium alloy, cobalt chrome alloy, niobium or tantalum. Also, the final metal foam and/or the solid substrate of the orthopedic implant also may be made of titanium, titanium alloy, cobalt chrome alloy, niobium or tantalum. Preferably, the final metal foam and the substrate are produced from titanium or titanium alloy.

In another aspect, the invention provides a method of forming a porous scaffold for use in an implantable medical device, that includes:

a) providing a first metal foam of biocompatible metal;

b) spraying an atomized mist of a binder solution on the first metal foam, wherein said mist has an average droplet size ranging from about 20 µm to about 80 µm;

c) delivering a plurality of metal particles to the metal foam;

d) bonding the metal particles to the first metal foam; whereby producing a second metal foam having smaller pore size than the first metal foam.

The steps (b), (c), and (d) may be repeated if desired. Preferably, the mist is produced by an ultrasonic source. The preferred average droplet size ranges from about 30 µm to about 40 µm. The preferred binder solution is an aqueous solution of methyl cellulose. Preferably, the metal of the first metal foam and/or of the metal particles is titanium, titanium alloy, cobalt chrome alloy, niobium or tantalum.

The invention also provides the second metal foam produced by the method(s) of this aspect of the invention. The preferred pore size of the second metal foam ranges from about 100 µm to about 1000 µm, more preferably, from about 300 µm to about 500 µm.

In yet another aspect, the invention provides a method of forming a porous scaffold for use in an implantable medical device, the method including:

a) providing a polymer foam having a pre-determined thickness and a first pore size;

b) forming a metal skin network of biocompatible metal on the polymer foam by low temperature arc vapor deposition;

c) decomposing the polymer foam in an inert gas atmosphere thereby forming a green metal foam;

d) pre-sintering the green metal foam;

e) contacting the pre-sintered metal foam with metal particles in the presence of a binder;

f) bonding the metal particles to the pre-sintered metal foam;

whereby obtaining the porous scaffold having pores of a second pore size.

Preferably, the pre-determined thickness of the polymer foam is from about 0.5 mm to about 2 mm. Also, preferably, the first pore size is from about 900 µm to about 1100 µm. The preferred second pore size is from about 300 µm to about 500 µm.

The preferred inert atmosphere is argon atmosphere. Preferably, the metal particles and the pre-sintered foam are bonded by sintering. The preferred metal of the scaffold is titanium, titanium alloy, cobalt chrome alloy, niobium or tantalum. The preferred metal of the metal particles is also titanium, titanium alloy, cobalt chrome alloy, niobium and tantalum.

In yet another aspect, the invention provides a method of improving stability of a porous scaffold in an orthopedic implant, that includes a) providing a pre-cursor for the orthopedic implant, the pre-cursor including a body and a spaced member attached to the body, the spaced member including a wall member spaced from the body and a spacer element connecting the wall member to the body thereby the spacer element, the body, and the wall member define a recess;

b) attaching the porous scaffold to the body, wherein the porous scaffold has a pre-determined pore size and includes a first portion and a second portion, which extends into the recess;

c) filling the recess, including the second portion of the porous scaffold, with metal particles having a particle size smaller than the pore size of the porous scaffold thereby the pores of the second portion of the porous scaffold are filled with the metal particles;

d) sintering the implant pre-cursor, the metal particles, and the attached porous scaffold including the filled second portion thereby converting the spaced member, including the filled recess to a substantially solid metal block, including converting the filled second portion of the scaffold to a substantially solid portion of the substantially solid metal block; whereby the substantially solid portion at least partially supports the first portion of the porous scaffold.

The method of this aspect of the invention may further include subjecting the pre-cursor with the filled spaced member to a vibrational treatment before sintering. The invention also provides an orthopedic implant produced by the method of this aspect of the invention.

In yet another aspect, the invention also provides a method of improving stability of a porous scaffold in an acetabular cup implant, the method including a) providing a blank acetabular cup shell, including a body having a top surface, the blank shell including a rim, the rim having a ledge and a wall spaced from the body of the blank acetabular cup shell thereby the ledge, the body, and the wall define a circular annular recess;

b) attaching the porous scaffold to the top surface of body, wherein the porous scaffold has a pre-determined pore size and includes a first portion and a second portion, the second portion of the scaffold extending into the circular recess;

c) filling the recess, including the second portion of the porous scaffold, with metal particles having a particle size smaller than the pore size of the porous scaffold thereby the pore of the second portion of the porous scaffold are filled with the metal particles;

d) bonding the particles to the ledge, the wall, the second portion of the porous scaffold, and to each other, thereby converting the rim to a substantially solid metal block, including converting the filled second portion of the scaffold to a substantially solid portion of the substantially solid block;

whereby the substantially solid portion at least partially supports the first portion of the porous scaffold.

Preferably, in the method of this aspect of the invention the bonding is effected through sintering.

The method of this aspect of the invention may further include machining the substantially solid block into a desired shape. The invention also provides the acetabular cup implant that includes an acetabular cup shell produced according to the method(s) of this aspect of the invention.

DESCRIPTION OF THE DRAWINGS

A more accurate appreciation of the subject matter of the present invention and the various advantages thereof can be realized by reference to the following detailed description, which makes reference to the accompanying drawings in which.

DESCRIPTION OF THE PREFERRED EMBODIMENTS

In accordance with one embodiment, the invention provides a porous metallic scaffold suitable for medical device application, especially for orthopedic implants. In the preferred variant, the porous scaffold of the invention is a high strength, open cell, metallic foam with pore sizes preferably above 100 μm, more preferably, ranging from about 100 μm to about 1000 μm, more preferably, ranging from about 300 μm to about 500 μm. The porous scaffold is also characterized by high pore volume, ranging from about 50% to about 90%, more preferably, from about 60% to about 80%. The scaffold has a porous surface. The porous surface interfaces with a bone if the porous scaffold is used in an orthopedic implant. The porous scaffold is preferably made from biocompatible metals, such as titanium, titanium alloys, cobalt-chrome alloy, tantalum, and niobium. The most preferred metals are titanium and titanium alloys. The preferred titanium alloy is Ti-6Al-4V alloy. The scaffold may be in a form of a block, a layer, a tissue in-growth surface or other desirable form or shape.

Figure 1:
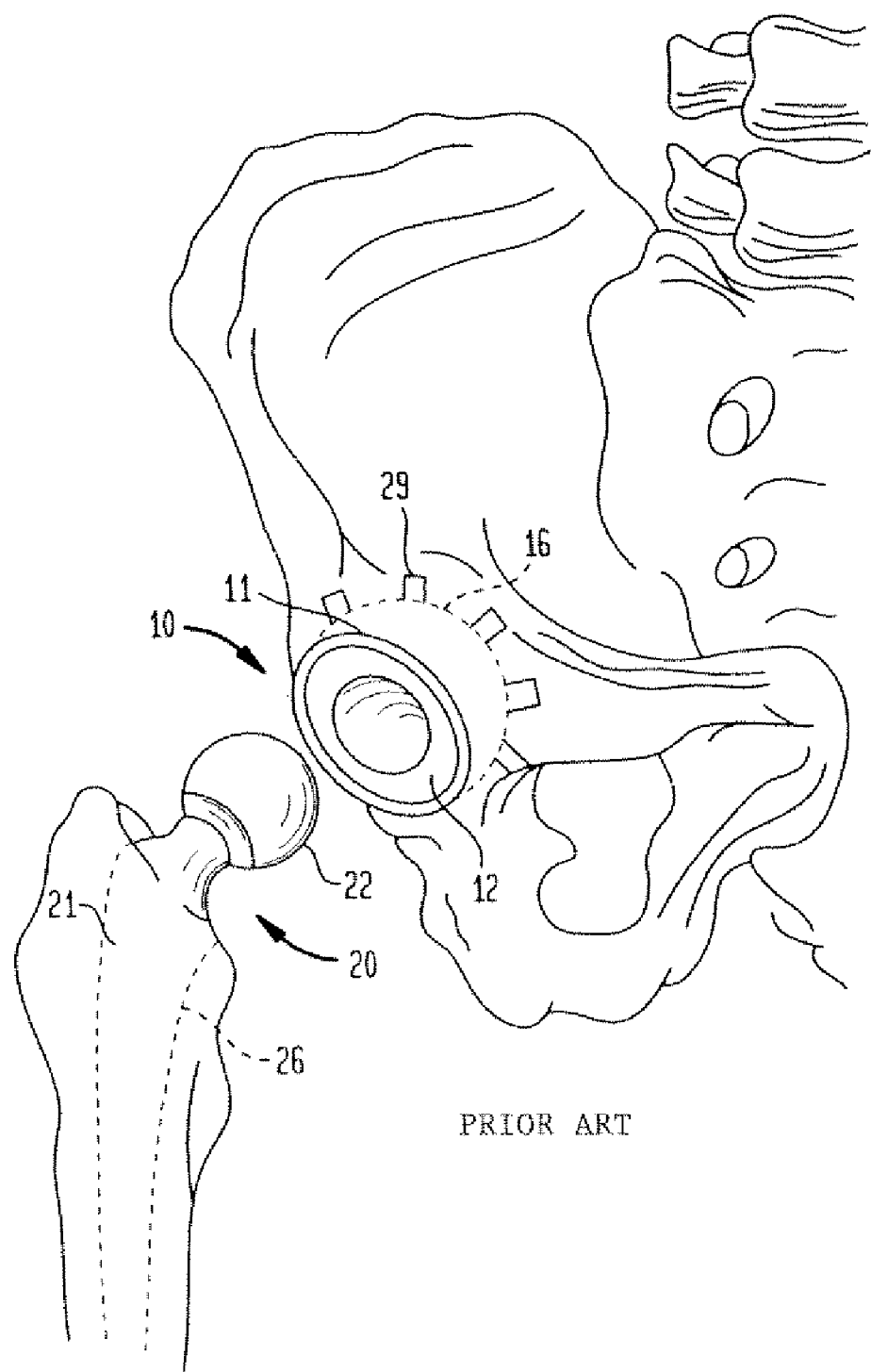
FIG. 1 shows a typical hip joint implant system.
Figure 2:
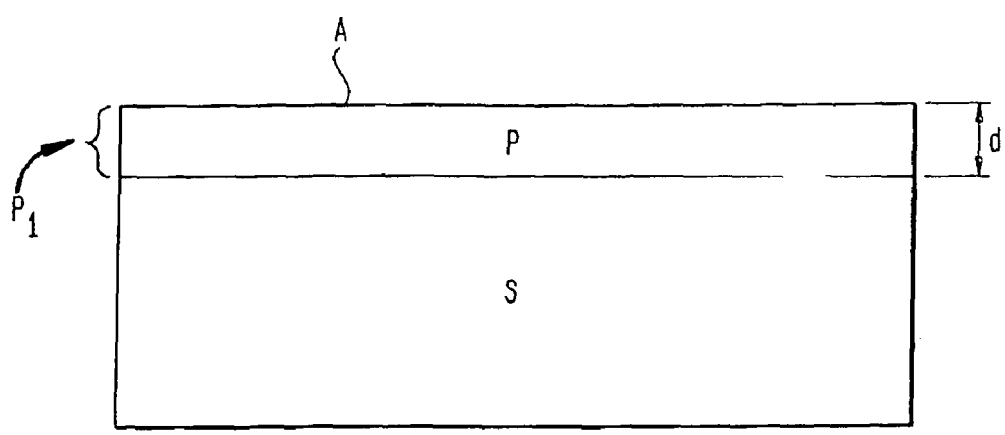
FIG. 2 illustrates one of the embodiments of a porous metal scaffold of the invention suitable for use in implantable medical devices.

The porous scaffold P may be attached to a substrate S (FIG. 2). Preferably, the substrate S is a solid metallic substrate. The substrate S and the porous scaffold P are preferably integrated with each other. FIG. 2 shows the scaffold P in the form of a porous layer $P_1$. It should be understood that the shape of the scaffold P and the substrate S shown in FIG. 2 is purely illustrative, and by no means limiting. The preferred thickness d of the porous layer $P_1$ is ranging from about 0.5 mm to about 10 mm, more preferably, from about 1 mm to about 5 mm, yet more preferably, from about 1 mm to about 2 mm. The thickness of the solid substrate S may be selected as desired. Preferably, the porous layer $P_1$ has a porous surface A with high surface roughness. An intermediate layer may be present between the substrate S and the porous layer $P_1$, for example, for the purposes of bonding the layer $P_1$ and the substrate S.

Preferably, the substrate S and the porous layer $P_1$ are produced from the same metal or alloys of the same metal. The preferred metals are biocompatible metals, such as titanium, titanium alloys, cobalt-chrome alloy, tantalum, and niobium. The most preferred metals are titanium and titanium alloys. The preferred titanium alloy is Ti-6Al-4V alloy.

The porous scaffold P, with or without the substrate S, is especially useful for medical device applications, such as orthopedic implants. For example, the preparation of titanium implants having a porous bone-contacting interface (or tissue in-growth surface) suitable for orthopedic applications presents a number of non-trivial technical challenges. In addition to high pore volume, the desirable porous layer for an orthopedic implant has a rough surface, good pore regularity, and integrated binding with the underlying solid substrate if such substrate is used. In the past, titanium porous layers that combine these desired properties had not been produced.

Thus, in another embodiment, the invention also provides an orthopedic implant that incorporates the porous scaffold P, which is included in the implant as a porous bone-contacting surface, porous block, porous layer or the like. Non-limiting examples of the implants that may include the scaffold P are an acetabular cup implant, vertebral implant, a femoral hip stem implant, femoral and tibial knee joint components, soft tissue attachments, bone defect fillers, shoulder implants, spacers, and any medical device or implant having a surface contacting a bone. In addition to the porous scaffold P, the implant may include a solid metallic substrate. Preferably, the solid substrate and the porous scaffold are integrated with each other without cement or any other external binding material. For example, an acetabular cup implant may include a solid shell bearing the scaffold as the bone-contacting porous surface, block or layer. The porous scaffold facilitates in-growth of bone tissue into the pores of the scaffold, contributing to a long useful life of the acetabular cup implant after implantation. Also, the porous surface of the scaffold preferably has high surface roughness, which promotes initial press-fit stability and provides greater frictional interference between the porous surface and the bone.

The advantages of the orthopedic implants having the porous scaffold P are related to the method of forming the scaffold. In another embodiment, the invention provides a process for forming porous scaffolds of medical devices, especially orthopedic implants.

Figure 3:
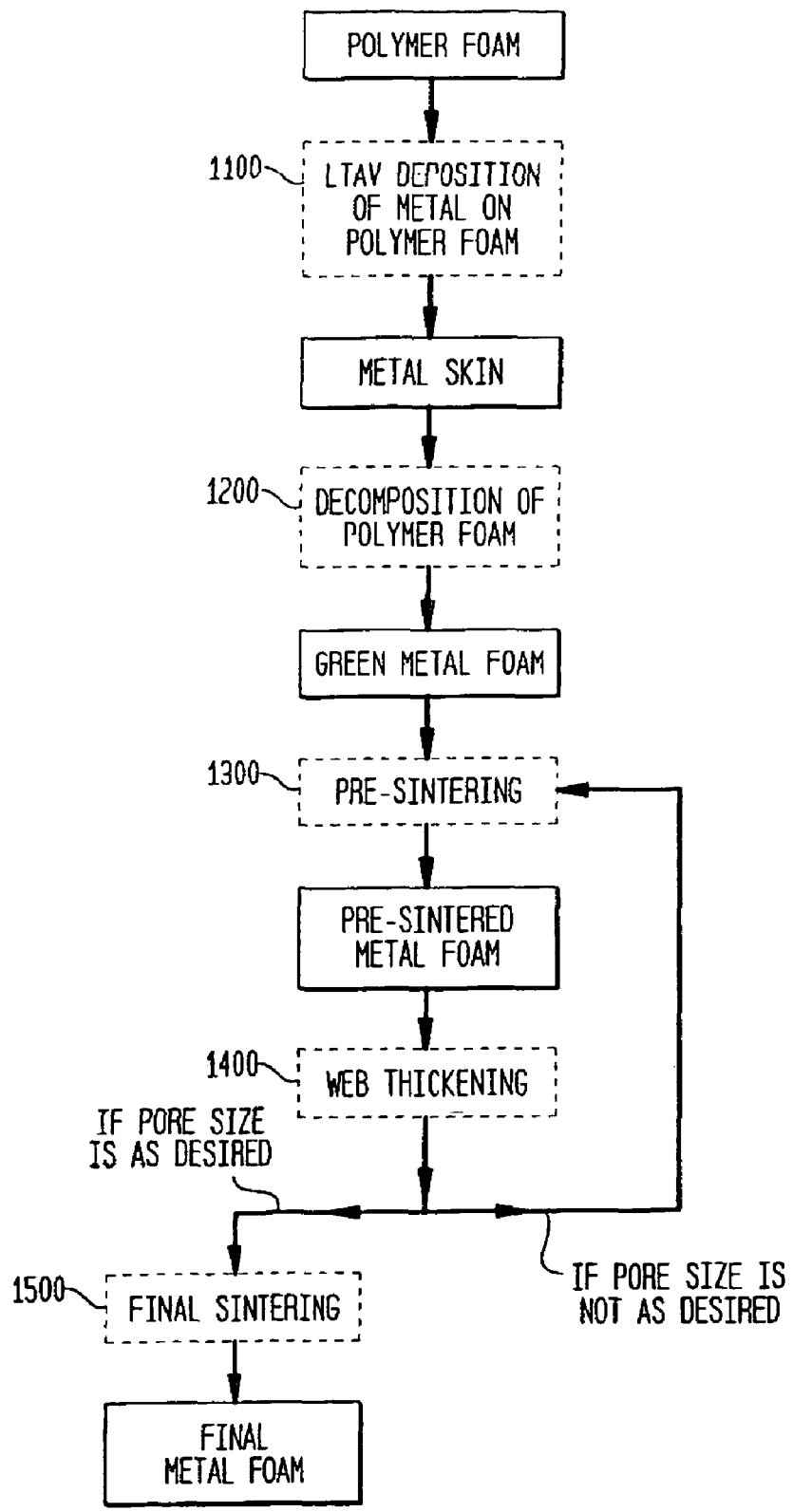
FIG. 3 shows a general functional block diagram of a method for producing porous metal scaffolds in accordance with one of the embodiments of the invention.

FIG. 3 shows a general scheme of the process. First, a desired biocompatible metal, such as titanium, is deposited on pyrolyzable polymer foam by low temperature arc vapor deposition (LTAVD or LTAV deposition) (Step 1100). LTAVD is a physical vapor deposition (PVD) method that utilizes a high current, low voltage electric arc to evaporate electrically conductive metals. The metal is evaporated in high vacuum and is deposited as a thin, highly adherent and dense coating on the desired substrate. The polymer foam includes a polymer web having an open cell, interconnected structure. The LTAV deposition creates a thin layer (or skin) of the metal on all surfaces of the polymer foam. Therefore, the structure of the deposited metal follows the structure of the polymer web, creating a metal skin over the polymer web. Controlling various parameters of LTAVD process, especially the time of the deposition, controls the thickness of the metal skin.

The polymer foam is a low density, high porosity polymer material. As described above, it serves as a template for the metallic porous layer to be formed. Preferably, the polymer foam is shaped in the same manner as the surface of the desired implant. The polymer foam may be placed around a solid portion of the future implant before deposition takes place. More preferably, however, the LTAV deposition is carried out on an unattached piece of the polymer foam. The preferable polymer foams decompose with minimal residual contamination upon heating. The foam made from pigmented polyurethane, which does not leave substantial residue upon decomposition, is preferred.

After the desired thickness of the metal skin is deposited, the polymer foam coated with the metal skin is heated at temperatures above the decomposition temperature of the polymer foam in an inert atmosphere (Step 1200). The polymer foam decomposes, leaving behind "green" metal foam, which is essentially the metal skin formed in the LTAVD deposition. The term "green" is used to refer to a metal foam that yet has not been strengthened by sintering or other similar techniques.

The next step is pre-sintering of the green metal foam (Step 1300). After pre-sintering, the green foam, which is the weak and thin metal skin, is build up to strengthen the metal foam and to obtain the desired porosity (Step 1400). The build up involves increasing the thickness of the internal surfaces of the pre-sintered foam, which may be termed web thickening. The preferred web thickening method involves applying one or more layers of metallic powder and binding it to the pre-sintered metal foam by powder metallurgy techniques. The web thickening may also be accomplished by LTAV deposition, high temperature PVD or chemical vapor deposition. The web thickening reduces the pore size of the metal foam since the thickness of the internal pore surfaces increase.

If a single web thickening step provides metal foam with desired characteristics, such as strength and pore size, the foam may be subjected to final sintering. If further web thickening is necessary, the foam is again pre-sintered and the web thickening step is repeated. After the last web thickening step, the metal foam having the desired thickness, strength, and porosity undergoes a final sintering step, preferably together with the underlying solid metallic substrate (Step 1500).

The process will now be described in more detail. The process will be described with reference to the formation of a titanium acetabular cup implant. However, it should be understood that other biocompatible metals, such as titanium alloys, cobalt-chrome alloys, niobium, tantalum and other metals might also be suitable. Likewise, it should be understood that similar methods might be used to produce other types of implantable medical devices.

To begin manufacturing of the implant, a piece of polyurethane foam having a desired thickness, and a shape matching the shape of the future implant's bone-interface surface is subjected to LTAV deposition of titanium. The properties of the polyurethane foam (e.g., porosity, density, and thickness) are important since they may be used to affect the properties of the final metallic porous layer. Thus, the thickness of the polyurethane foam determines the thickness of the porous metal layer. In the preferred embodiment, the polyurethane foam has thickness ranging from about 0.5 mm to about 10 mm, more preferably, from about 1 mm to about 5 mm, yet more preferably, from about 1 mm to about 2 mm. Also, the porosity of polyurethane foam may be used to control pore size and pore volume of the green metal foam and the final porous metal layer. Preferably, the polyurethane foam has pore sizes over 500 µm, more preferably between about 800 µm and about 2000 µm, most preferably, between about 900 µm and about 1100 µm.

As described above, to facilitate bone in-growth, the porous layer of the implant preferably has pores size of 100 µm or more. However, if the pore size of the final metal foam is too large, the porous layer may become weak because of insufficient structural strength. And, of course, if the pore size is too small, the in-growth of the bone or other tissue may be retarded. The process of this embodiment of the invention first produces the weak green foam with large pore size, and then reduces the pore size in the web thickening step. This methodology allows good control over the desired pore size and process conditions. The proper balance between strength and in-growth potential is achieved by selecting a combination of porosity of the polyurethane foam and web thickening conditions.

The porosity of the polyurethane foam directly affects the pore size of the green metal foam and limits the maximum possible pore size of the final porous layer. In an illustrative non-limiting example, polyurethane foam with porosity of 58 pores per cubic inch (ppi) and pore size of 1100 µm may be processed by coating with metal powder to yield final metal foam with pore size of about 600 µm. Under identical processing conditions, the polyurethane foam with porosity of 48 ppi and pore size of 1400 µm yields a final metal foam with the pore size of about 900 µm.

Another method to control the pore size of the final foam is to vary the number of applications of the titanium powder, which is applied to thicken the green metal foam. The same goal may be accomplished by varying the particle size of the titanium powder. However, it should be understood that if the particle size of the powder is too large, the particles may not be able to penetrate into the pores of the metal foam.

In another illustrative non-limiting example, 1100 µm polyurethane foam may require two powder layers to produce 600 µm pore size. Increasing the number of powder layers to three decrease the final metal pore size to approximately 400 µm, while applying only one layer of powder would result in final pore size of approximately 800 µm. The thickness and the required number of layers of the metal powder may be affected by the characteristics of the powder particle, such as average size, shape and particle size distribution.

To a lesser degree, the thickness of the initial LTAVD coating may also be varied to affect the pore size of the final metallic foam. In an illustrative non-limiting example, a titanium coating with the thickness of 25 µm applied by LTAVD to the polyurethane foam with the pore size of 1100 µm could contribute to a metal foam with a pore size of 600 µm. If the thickness of the LTAVD coating is increased to 50 µm and all other process parameters are kept the same, the pore size of the final metal foam would decrease to approximately 550 µm.

Figure 4A:
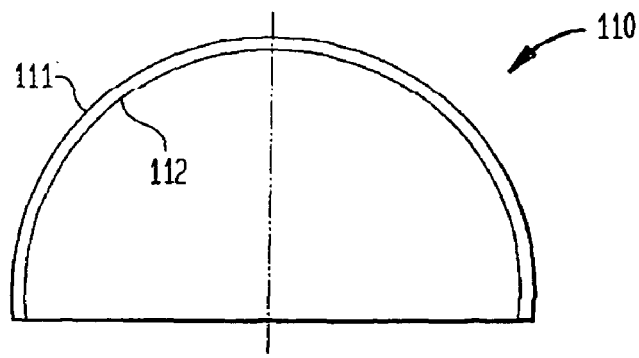
FIGS. 4A and 4B show an example of a polyurethane shell that matches the shape of an acetabular cup shell in accordance with one embodiment of the invention.
Figure 4B:
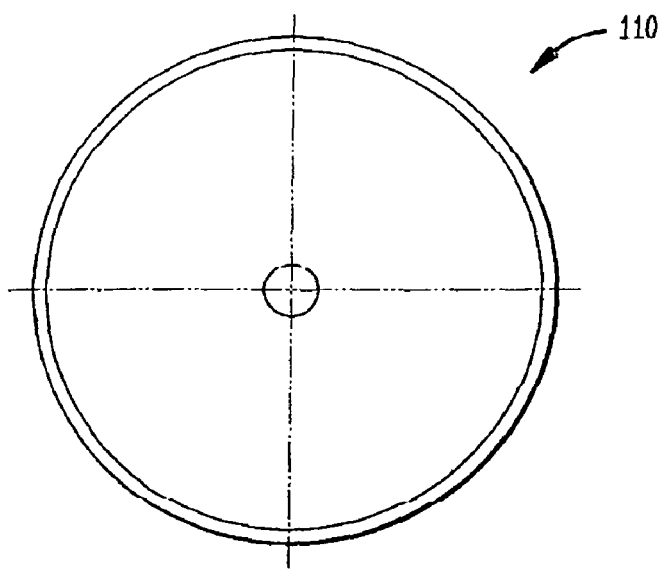

FIGS. 4A and 4B show a polyurethane foam shell 110 suitable for producing a porous layer of an acetabular cup implant. As seen from FIG. 4A, the shell 110 matches the shape of a shell of an acetabular cup implant. The polyurethane foam shell 110 has a first side 111 and a second side 112. The preferred thickness of the shell 110 is from 1 mm to 2 mm. The shell 110 is subjected to LTAV deposition of titanium. The preferred conditions for LTAV deposition of titanium on polyurethane foam is vacuum of less than $10^{-4}$ torr and electric current setting of 130 amperes. LTAVD methodology is described in greater details in U.S. Pat. Nos. 4,351,855, 4,975,230, and 5,011,638, which are incorporated herein by reference in their entirety. In general, the process of the invention uses conventional LTAVD methodology. The above-identified patents may be consulted for additional information.

Figure 4C:
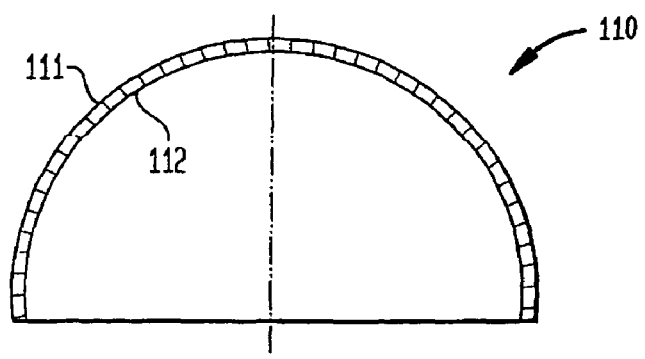
FIG. 4C illustrates a titanium-coated polyurethane shell shown in FIGS. 4A and 4B.
Figure 5:
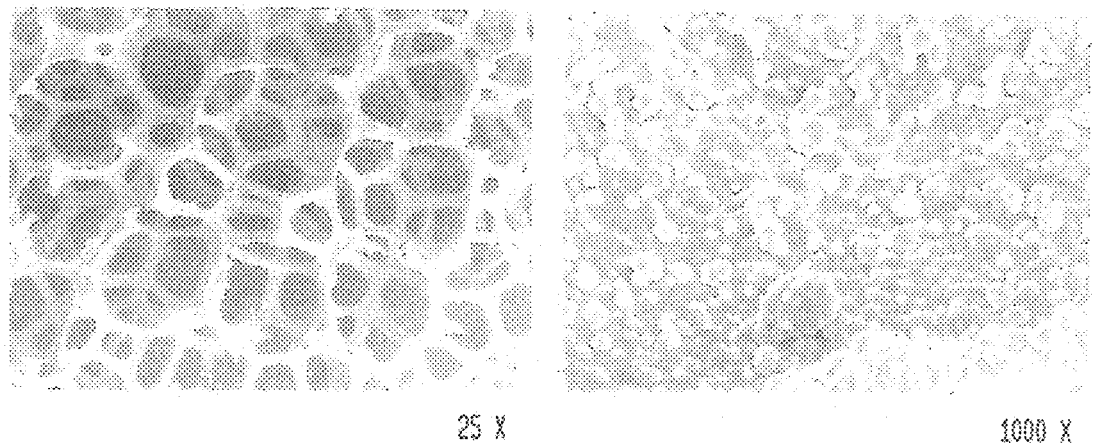
FIG. 5 shows scanning electron microscope (SEM) photographs of the titanium-coated polyurethane foam at 25× and 1000× magnifications.

LTAV deposition produces a titanium-coated polyurethane shell 110A (FIG. 4C). The deposition creates a titanium skin within the polyurethane foam. FIG. 5 is a scanning electron microscope (SEM) photograph of the titanium-coated polyurethane foam at 25× and 1000× magnifications. The titanium skin coats internal and external surfaces of the polymer web. Preferably, the thickness of the titanium skin is from about 1 μm to about 50 μm. More preferably, the thickness of the titanium skin is ranging from about 10 μm to about 35 μm. Most preferably, the thickness of the titanium skin is approximately 10 μm for the first side 111, and about 35 μm for the second side 112 of the shell 110. In the LTAVD process, the thickness of the titanium skin is varied by turning over the polyurethane foam shell and coating the second side 112 for longer period of time.

Figure 6:
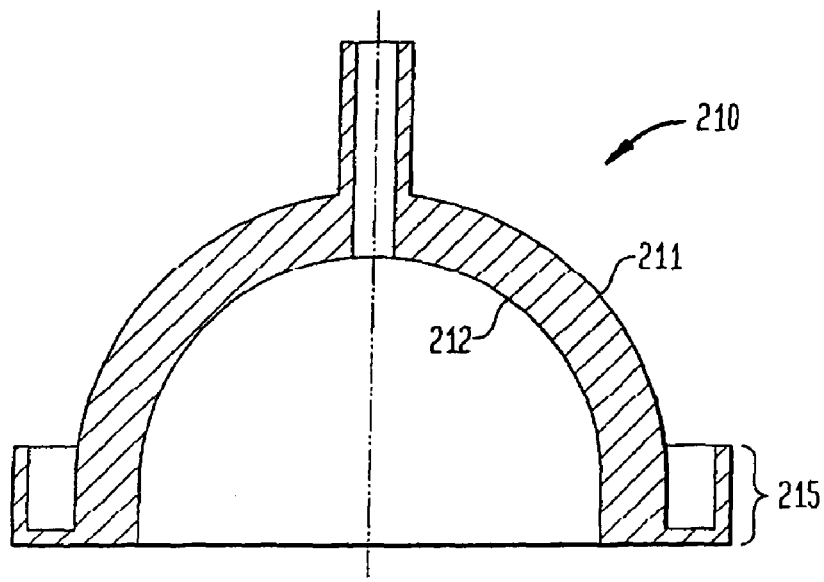
FIG. 6 shows a schematic front cross-sectional view of a blank shell of an acetabular cup implant in accordance with the preferred embodiment of the invention.
Figure 7:
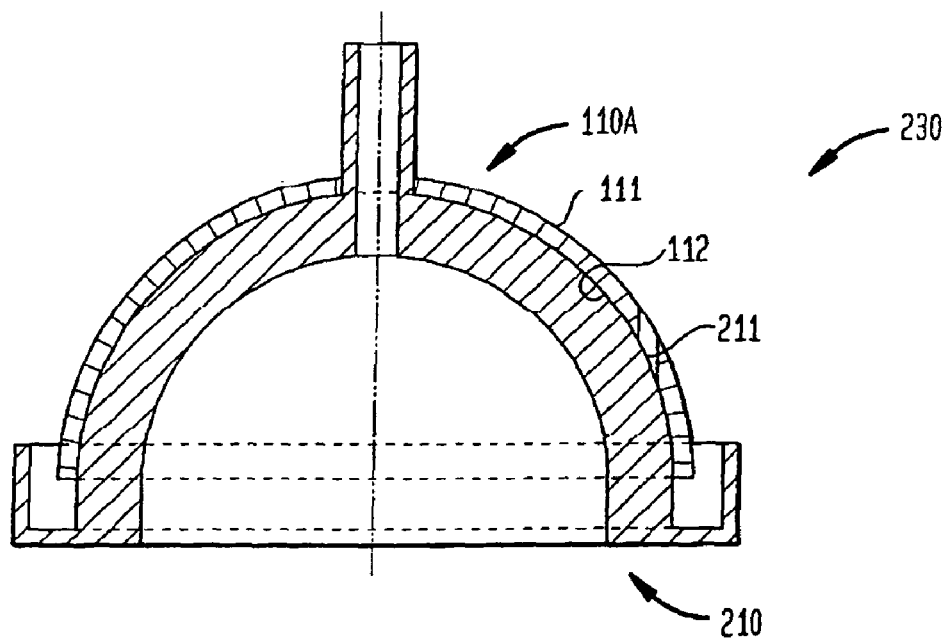
FIG. 7 shows a schematic front cross-sectional view of an assemblage of the blank shell of an acetabular cup implant and the titanium-coated polymer foam in accordance with the preferred embodiment of the invention.

A blank metal shell 210 of an acetabular cup implant serves as a substrate for final metal foam (FIG. 6). The blank shell 210 is made from solid titanium. The blank titanium shell 210 has a top surface 211 and a bottom surface 212 (FIG. 6). After the LTAV deposition, the titanium-coated polyurethane foam shell 110A is wrapped around the blank shell 210 with the second side 112 of the coated polyurethane foam shell 110 facing the top surface 211 of the blank titanium shell 210 (FIG. 7). Then, an assemblage 230 of the blank shell 210 and the attached shell 110A is heated to decompose polyurethane.

Figure 8:
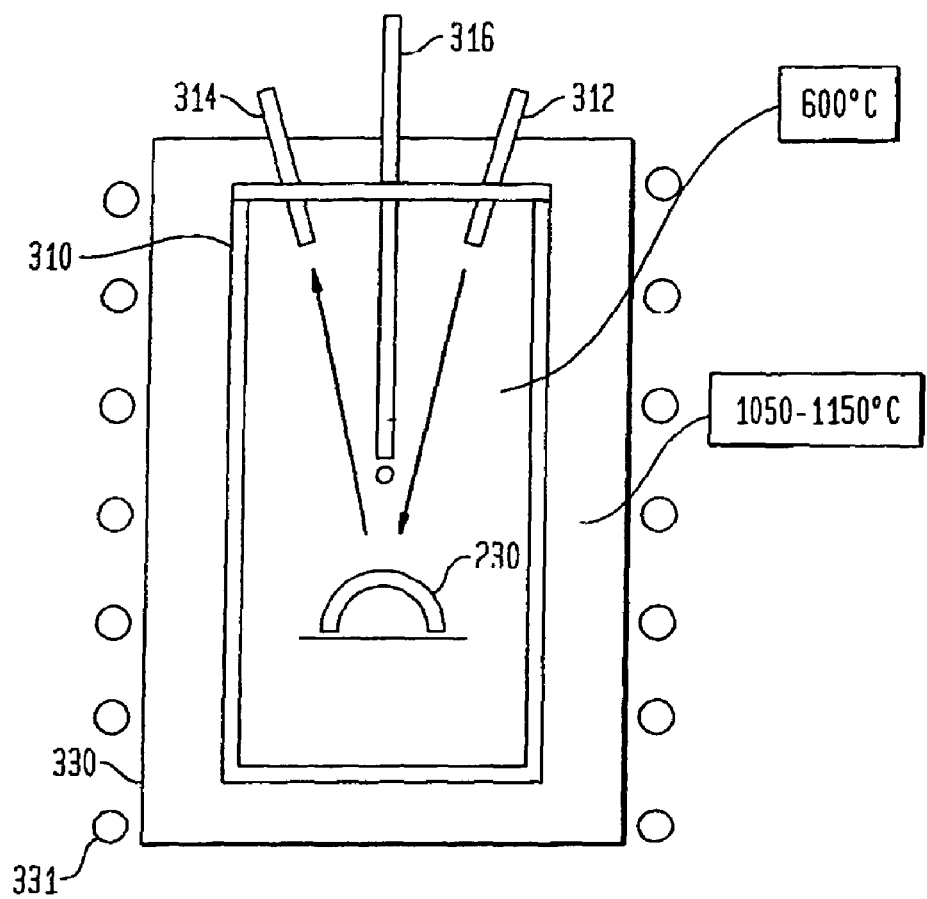
FIG. 8 shows a scheme of the furnace set-up for decomposing polyurethane foam in accordance with the preferred embodiment of the invention.

The preferred heating set up is shown in FIG. 8. As seen from FIG. 8, the assemblage 230 is placed in a retort 310 equipped with an argon inlet 312, a gas exhaust 314, and a thermocouple 316, purged with argon, and transferred to a furnace 330. The furnace 330 is equipped with heating elements 331. Inside the furnace 330, the assemblage 230 is maintained under the argon atmosphere to prevent oxidation of titanium.

The furnace 330 is maintained at a temperature substantially above the decomposition temperature of polyurethane (177° C.). The preferred furnace temperature is from about 1050° C. to about 1150° C., the more preferred furnace temperature is from about 1055° C. to about 1075° C. Because of the high temperature in the furnace, the assemblage 230 is rapidly heated, decomposing polyurethane in the shell 110A.

The decomposition of polyurethane results in a build-up of decomposition gases inside the titanium skin of the shell 110A. Referring to FIG. 7, the decomposition gases rupture the titanium skin on the first side 111 of the shell 110A, creating cracks to allow gases to escape. The inventors found that the thickness of titanium skin of the side 111 is important to control the escape of the decomposition gases. The inventors also found that it is important to rapidly heat the assemblage 230. Rapid heating is believed to contribute to minimizing residue.

Once the temperature inside the retort 310 exceeds the decomposition temperature of polyurethane by about 400° C., the burn-off cycle is complete. The complete polyurethane burn-off takes approximately 5 to 10 minutes. The retort 310 is removed from the furnace 330, and the assemblage 230 is allowed to cool to room temperature in an argon atmosphere.

Figure 9:
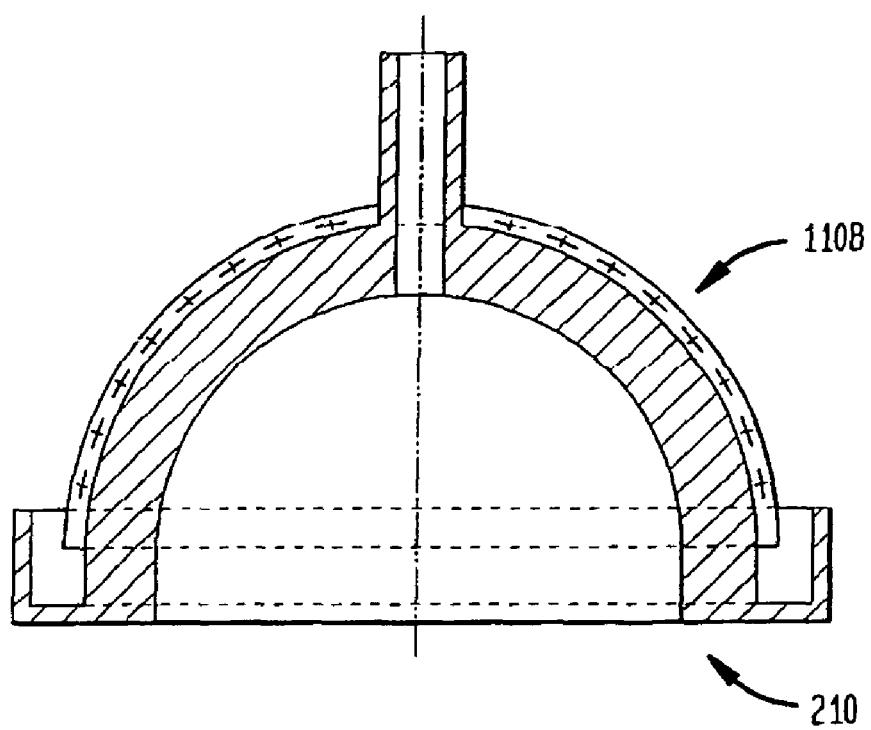
FIG. 9 shows a schematic front cross-sectional view of the blank shell of an acetabular cup implant having a green titanium foam in accordance with the preferred embodiment of the invention.
Figure 10A:
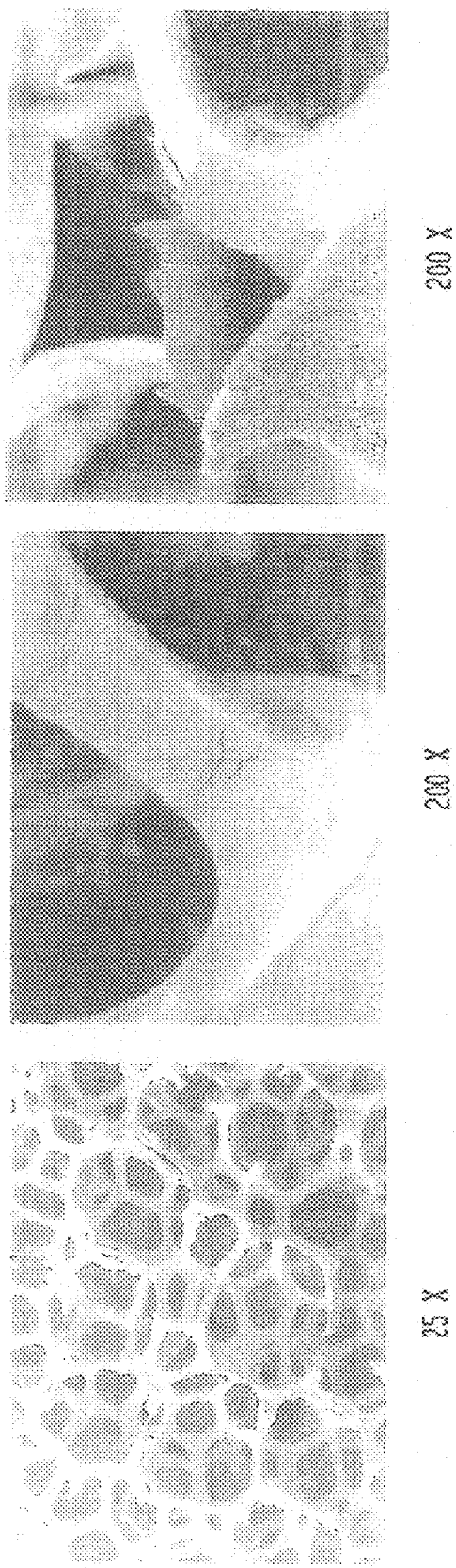
FIG. 10A shows scanning electron microscope photographs of a green titanium foam at 25× and 200× magnifications.

The burning off of polyurethane produces green titanium foam 110B on the surface of the shell 210 (FIG. 9). FIG. 10A shows a SEM photograph of the green titanium foam after removal of the polyurethane foam. The green titanium foam typically has pores similar to or slightly larger than the pores of the starting polyurethane foam. Typically, the green titanium foam has pore sizes 1% to 5% greater than the pore sizes of the polyurethane foam, often about 3% greater. For example, if the pore size of the polyurethane foam of the shell 110 is 1000 μm, the pore size of the green titanium foam 110B may be 1000-1050 μm.

Figure 10B:
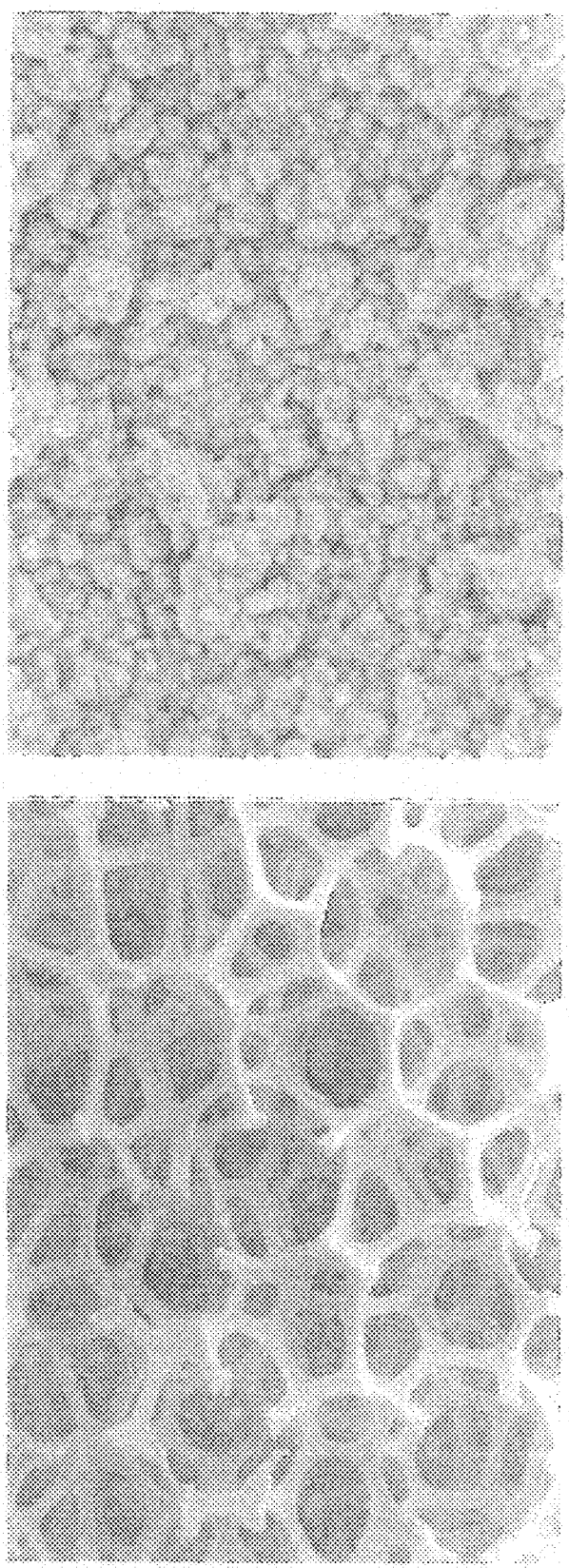
FIG. 10B shows scanning electron microscope photographs of a pre-sintered titanium foam at 25× and 1000× magnifications.

The green titanium foam 110B is fragile. To strengthen the green foam before it can be thickened to the desired pore size/pore volume, the assemblage is pre-sintered in a conventional lab furnace. The preferred pre-sintering temperature is from about 1260° C. to about 1370° C., more preferably, it is about 1315° C. After pre-sintering, the green foam may now be used for further processing. FIG. 10B shows a SEM photograph of the pre-sintered titanium foam.

The next step in the process is to thicken and strengthen the titanium foam and to achieve a desired pore volume and pore size. The more preferred pore size for the porous layer of an implant is from about 300 μm to about 500 μm. In one variant, LTAVD process may be used to extend the titanium web. Preferably, the titanium web is extended through a powder metallurgy process. Powder metallurgy involves binding metal particles into a solid whole and/or applying a metal powder to a surface, usually a metallic surface, and bonding the powder to the surface by heating.

Figure 11:
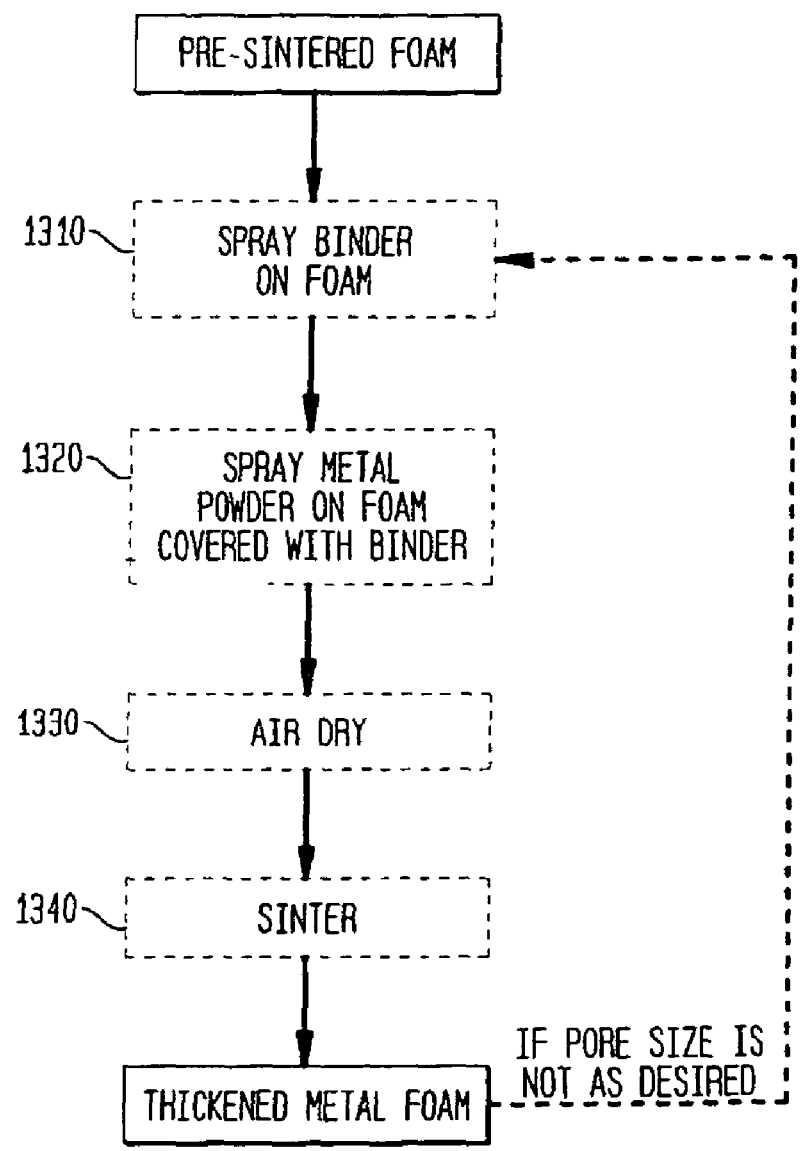
FIG. 11 is a functional block diagram of the preferred variant of the web thickening process in accordance with the preferred embodiment of the invention.

A scheme of the preferred powder metallurgy process is illustrated in FIG. 11. The pre-sintered metal foam is sprayed with a solution of a binder (Step 1310). The binder is used to provide a temporary bond between the surfaces of the pre-sintered foam and external titanium powder. Preferably, an atomized (ultra fine) binder, preferably in the form of a mist, is delivered to the foam by an ultrasonic atomizing nozzles system. A layer of binder forms on all internal and external surfaces of the pre-sintered foam. In the most preferred embodiment, the nozzle employs a high frequency (e.g., 65 KHz) sound wave to atomize the solution of the binder into droplets with an average size of from about 20 μm to about 80 μm, more preferably, from about 30 μm to about 40 μm, and to deliver the droplets to the foam at a velocity of from about 0.6 to about 1.2 fps. Because of the small size of the binder droplets, the binder reaches substantially every surface inside and outside the titanium foam. Also, the use of the ultrasonically-produced ultra fine binder allows delivery of the binder inside the foam without bridging the pores.

Any binder suitable for orthopedic applications, such as fish glue and the like may be used. The preferred binder is a 2% aqueous solution of methyl cellulose with a viscosity of approximately 25 cps. Methyl cellulose leaves less carbon residue on the titanium foam than a fish glue after the binder is decomposed in sintering.

After the binder is sprayed, a powder of titanium particles is sprayed on the foam covered with the binder (Step 1320). It is desired to deliver the powder to every surface of the foam. For this reason, the size of the titanium particles is smaller than the pore size of the metal foam so that the particles may reach inside the foam without bridging the pores. The preferred titanium powder has a particle size of from about 20 μm to about 100 μm, more preferably from about 40 μm to about 80 μm. A powder spray delivery system is used to increase the particle momentum so that the particles may get into the bottom layer of the pre-sintered foam. As the titanium powder comes in contact with the foam, the binder ties the powder to the surfaces of the foam. After the powder is applied, the excess of the powder is removed by air spraying (Step 1330), and the metal foam is sintered (Step 1340), producing thickened metal foam with pores smaller than the pores of the metal foam before web thickening. If the desired pore size is achieved with a single application of titanium powder, the sintering may be final and the thickened foam is the final metal foam. Alternatively, the foam is subjected to another pre-sintering, and the binder spraying/powder application is repeated until the desired pore size is obtained.

The final sintering is used to improve the strength of the porous layer and the bond between the porous layer and the underlying solid substrate. After the final sintering, the metal foam is integrated with the underlying substrate into a unitary component. Preferably, the final sintering is carried out under high vacuum with 9° C. per minute ramp rate. The preferred temperature for final sintering is from about 1425° C. to about 1530° C., more preferably, the final sintering is done at approximately 1500° C.

Figure 12:
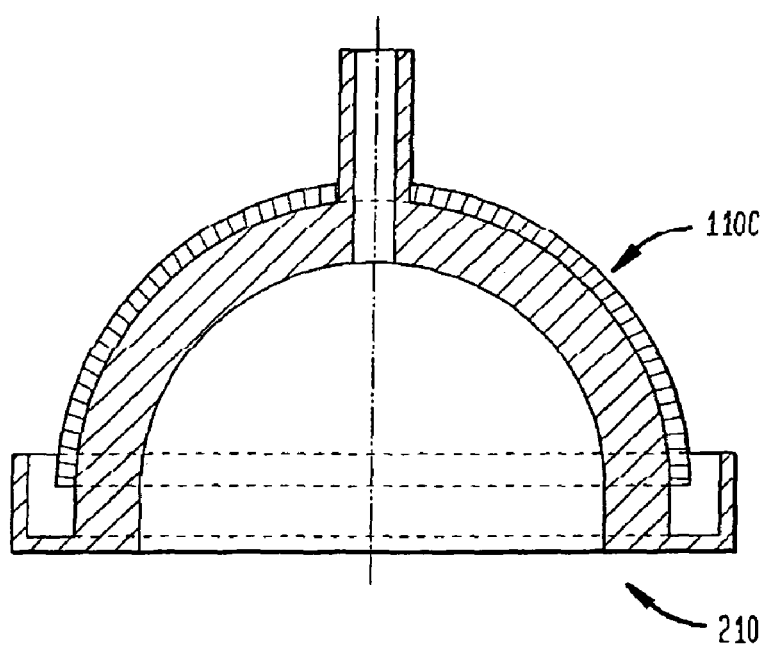
FIG. 12 shows a schematic front cross-sectional view of the blank shell of an acetabular cup implant having a thickened titanium foam in accordance with the preferred embodiment of the invention.
Figure 13:
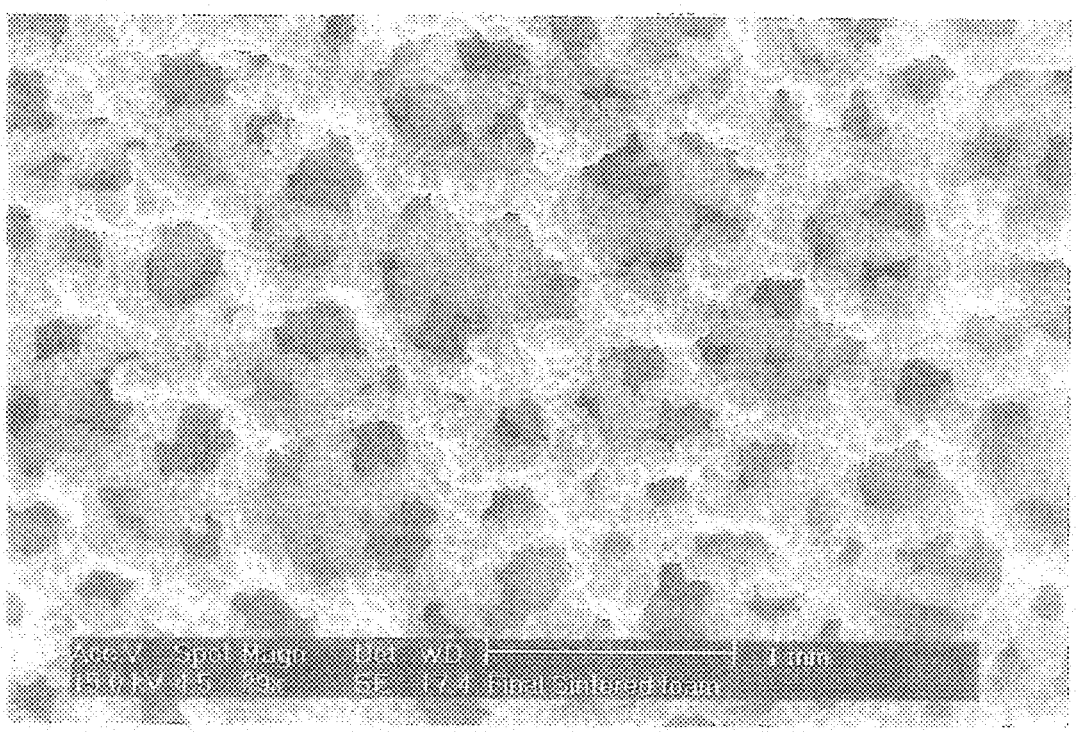
FIG. 13 shows an SEM photograph of the final titanium foam shown at 25× magnification.

The web thickening converts the foam 110B into a thickened foam 110C (FIG. 12). As described above, the process of the invention may include one, two or more web thickening steps. Thus, the thickened foam 110C may be the final metal foam or an intermediate foam. FIG. 13 shows a SEM photograph of the final titanium foam (porous layer for an implant) shown at 25× magnification. The final porous titanium foam preferably has the pore volume from about 50% to about 90%, more preferably from 60 to 80%, and the pore size from about 100 μm to about 1000 μm, more preferably, from about 300 μm to about 500 μm. If desired, the final metal foam may be coated with a biocompatible coating.

In other embodiments, the invention also provides an acetabular cup implant that incorporates a porous metallic layer and a preferred structure of such implants, as well as a method of making such acetabular cup implant that improves adhesion and stability of the porous metallic layer.

Figure 14A:
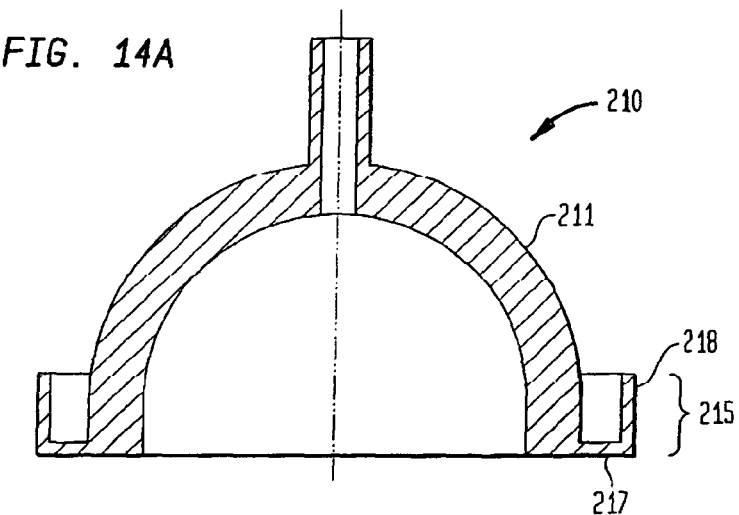
FIGS. 14A-14B illustrate a blank shell of an acetabular cup implant having a rim in accordance with the preferred embodiment of the invention.
Figure 14B:
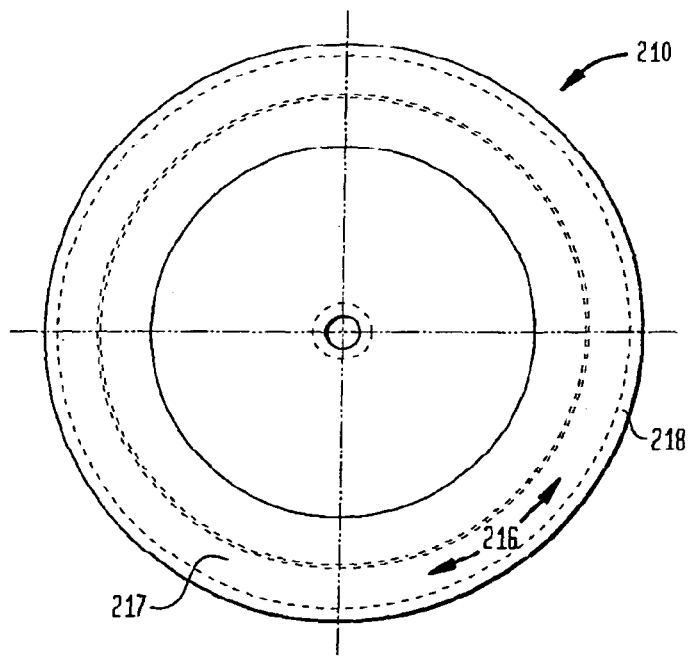
Figure 14C:
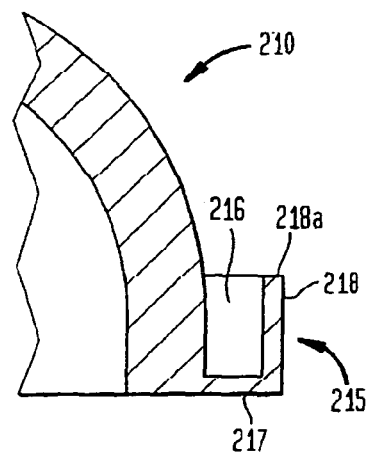
FIG. 14C shows the rim of the acetabular cup implant in accordance with the preferred embodiment of FIGS. 14A-14B.
Figure 15A:
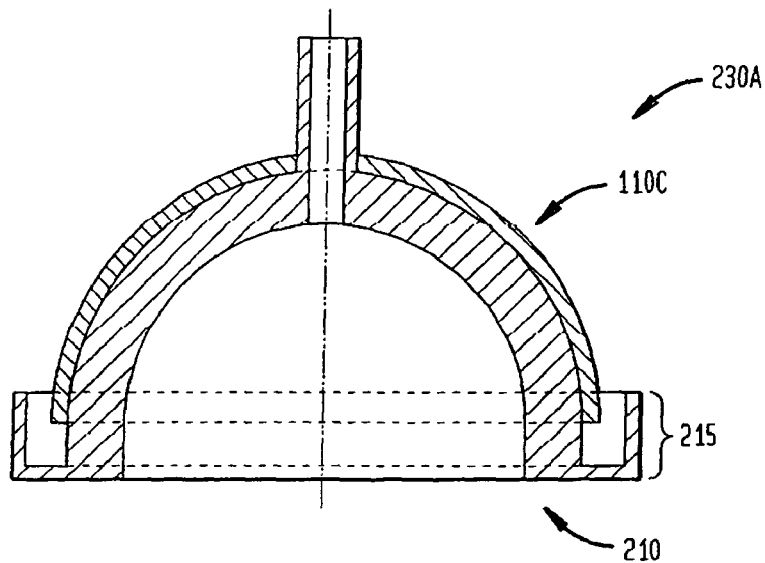
FIG. 15A-15C illustrate an acetabular cup shell having a thickened titanium foam, and the filling of the rim of the blank shell shown in FIGS. 14A-14C in accordance with the preferred embodiment of the invention.
Figure 15B:
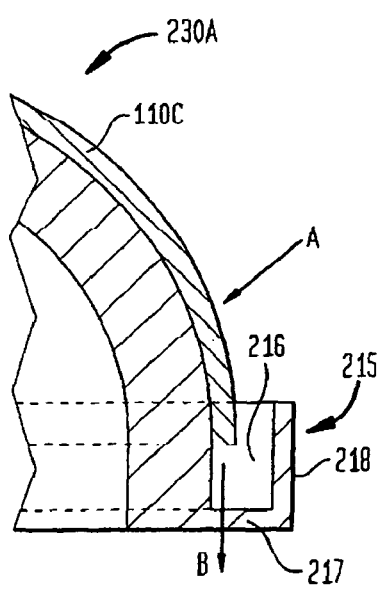

In the preferred embodiment, the metal foam 110C is not immediately subjected to final sintering. Instead further processing is carried out to improve the stability of the metal foam. Referring back to FIG. 6, the blank titanium shell 210 may have a rim 215. FIGS. 14A-14C show additional details of the structure of the rim 215. The rim 215 includes a ledge 217 and a wall 218 (FIGS. 14A and 14B). The wall 218 has a top surface 218a (FIG. 14C). The ledge 217, the wall 218 and a section of the shell 210 define a recess 216 (FIG. 14C). After the blank shell 210 is processed as described above, the porous foam 110C and the shell 210 are integrated into a unitary component 230A having the rim 215 (FIGS. 15A and 15B). When an acetabular cup implant having the foam 110C is implanted, significant forces are exerted upon the foam, for example as shown by the arrow A (FIG. 15B). If the foam 110C is not supported from below, the application of such forces may lead to disintegration of the foam, for example as shown by the arrow B. Therefore, in the preferred embodiment, the component 230A is further processed to improve stability of the porous metallic foam 110C. It should be understood that similar methods might be used for other implantable medical devices.

Figure 15C:
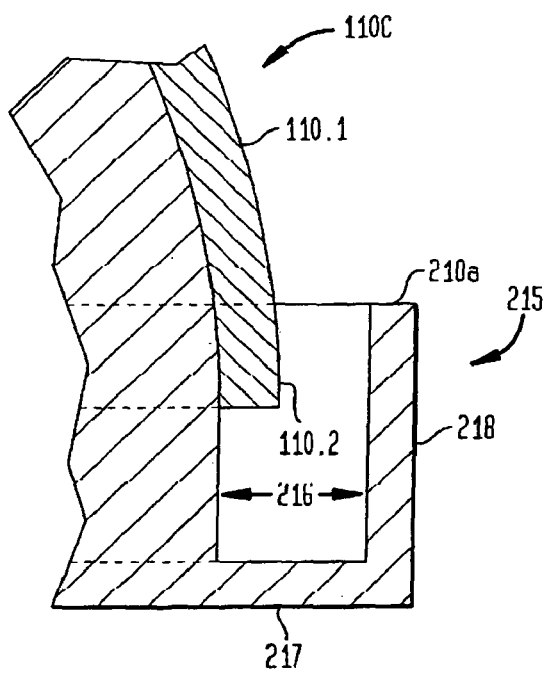

Referring to FIG. 15C, the foam 110C has sections 110.1 and 110.2. The section 110.2 extends into the recess 216 below the top surface 218a of the wall 218. The component 210A is sprayed with a binder, and the rim 215 is immersed into titanium powder approximately at the level of the top surface 218a of the wall 218. The immersion causes the powder to fill the recess 216. The particle size of the powder is selected so that the powder may enter into the pores of the foam 110C. Most of the section 110.1 of the foam 110C is not immersed in the powder. However, the section 110.2 is below the powder fill level (top surface 118a). Thus, the powder fills both the recess 216 and the pores of the section 110.2. A vibrational treatment may be used to facilitate the filing of the pores in the section 100.2 of the foam 110C.

Figure 16A:
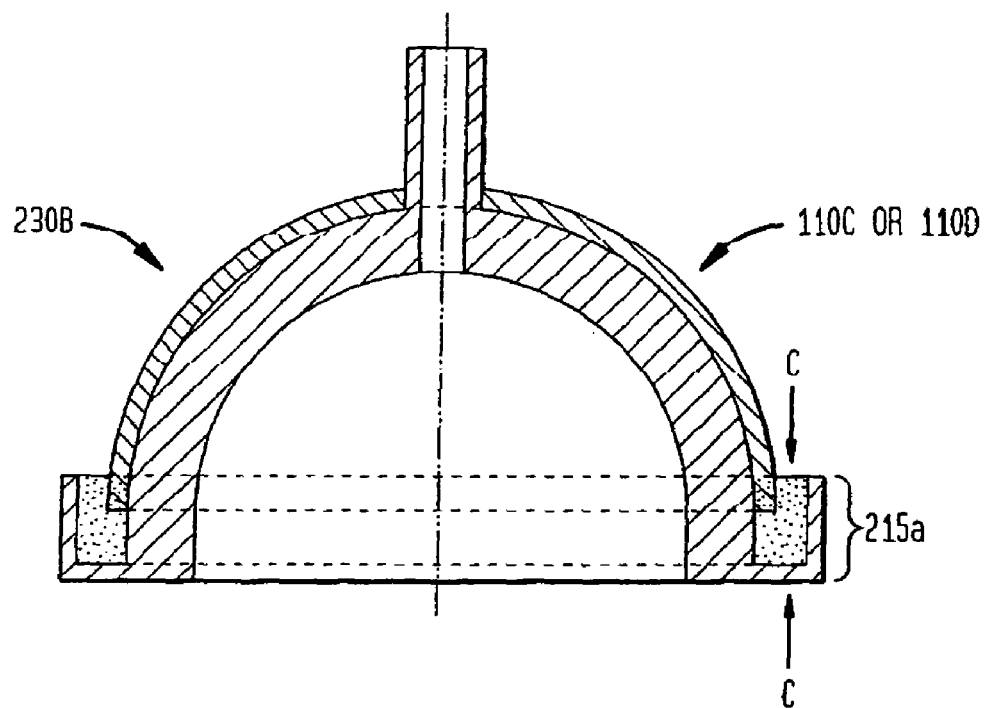
FIGS. 16A-16B, 17A-17B, and 18A-18B further illustrate filling of the rim of the shell shown in FIGS. 14A-14C and 15A-15C in accordance with the preferred embodiment of the invention.
Figure 16B:
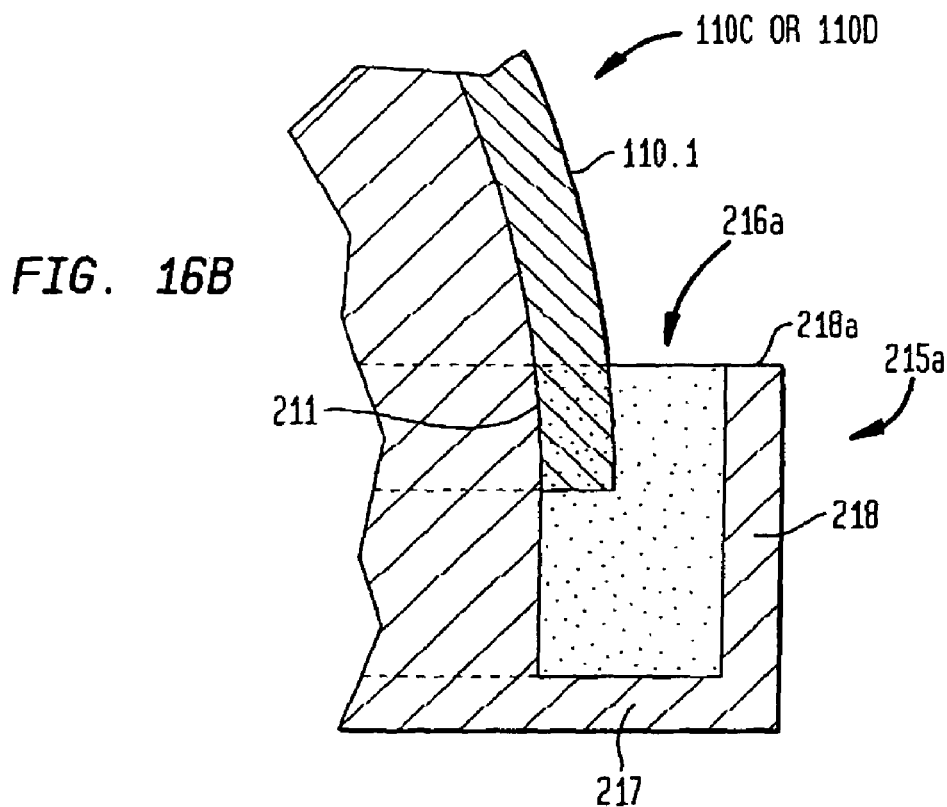

Once the rim 215 is full, the component 230A is subjected to final sintering, producing a component 230B having a filled rim 215a (FIGS. 16A and 16B). In one variant, the filling of the rim 215 may be combined with additional web thickening step. If so, upon final sintering, the foam 110C is converted to a thicker final titanium foam 110D (FIG. 16A). In another variant, the foam 110C may be the final titanium foam.

As seen in FIG. 16B, in the component 230B, the prior opening 216 and the section 110.2 are converted to a substantially solid metal block 216a, while the section 110.1 of the final foam 110C or 110D remains porous. The block 216a is integral with the surface 211 of the starting blank shell 210, the ledge 217, and the wall 218. The block 216a supports the metal foam 110C or 110D, providing improved stability for the metal foam.

Figure 17A:
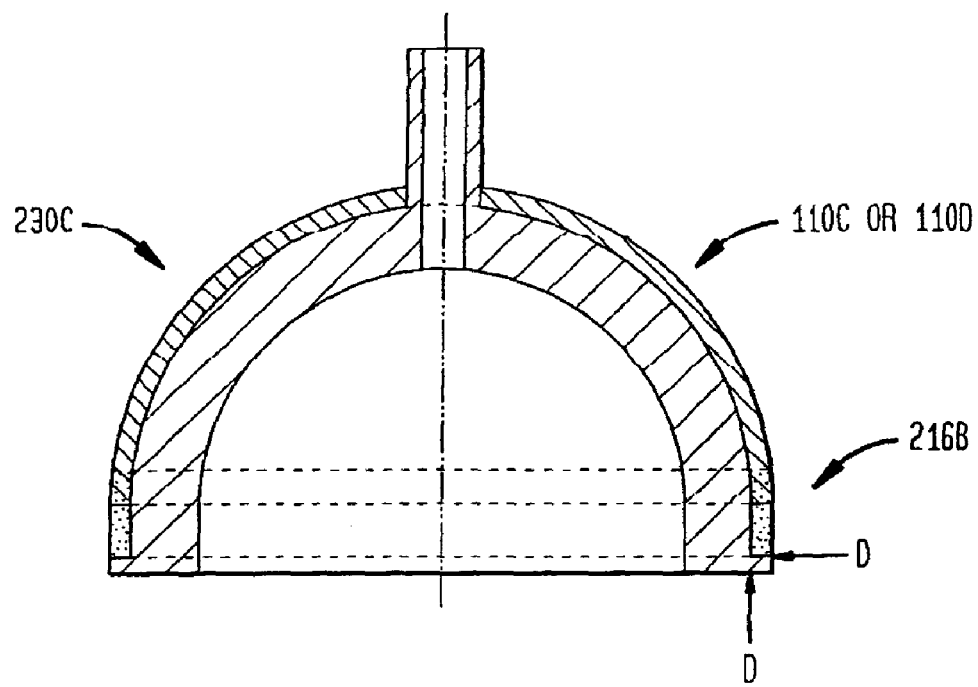
Figure 17B:
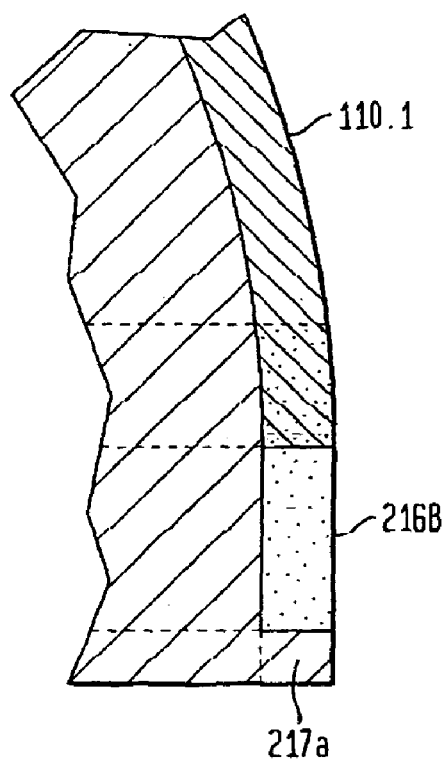
Figure 18A:
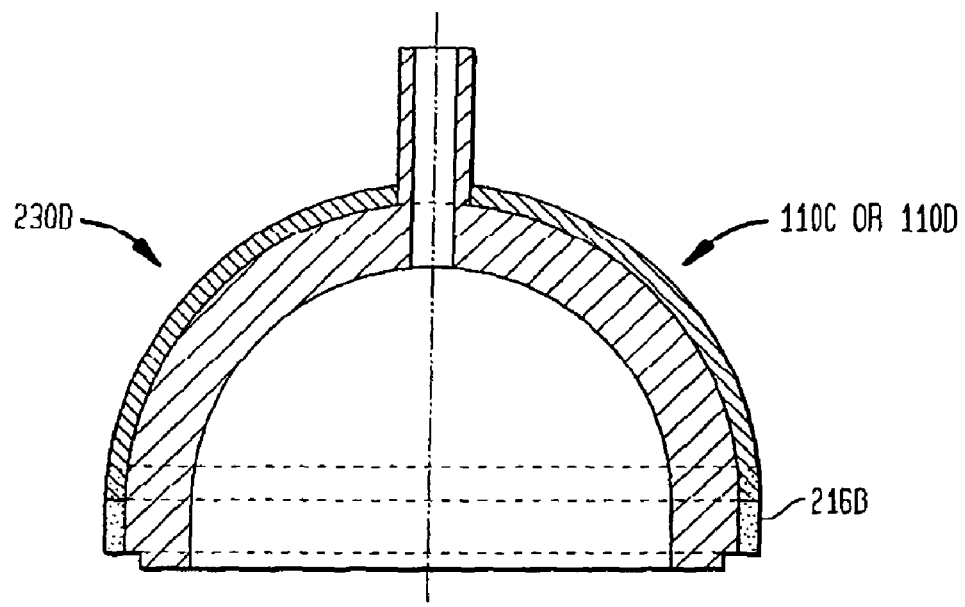
Figure 18B:
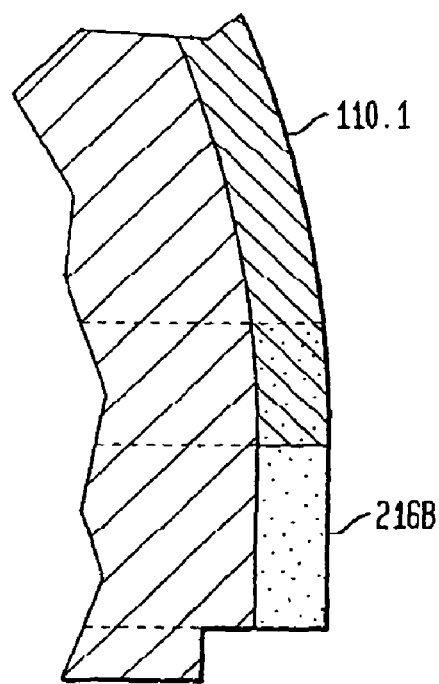

Generally, the component 230B, especially the filled rim 215a, may be machined as desired to obtain a shell of an acetabular cup implant having a desired shape and/or dimensions. For example, after final sintering, the component 230B may be machined as shown by arrows C in FIG. 16A. The machining removes portions of the rim 215 and the block 216a, and produces a component 230C shown in FIGS. 17A-17B. As seen in FIG. 17B, the block 216a is converted into a substantially solid layer 216b, which lies above a ledge portion 217a. After machining, the layer 216b supports the metal foam 110.1 (FIG. 17B). The ledge portion 217a may be removed by further machining, for example as shown by arrows D in FIG. 17A. In the resulting machined component 230D (FIGS. 18A and 18B), the final metal foam is supported by the substantially solid layer 216b.

EXAMPLE 1

Preparation of an Acetabular Cup Implant

It should be understood that while an acetabular cup implant is illustrated, this should not be considered a limitation on the scope of the invention.

A. Formation of Green Foam.

A block of polyurethane (PU) foam (Foamex, 950 μm, 58±2 ppi) is machined to a thickness of 1.5 mm and desired size and shape matching a shell of an acetabular cup. The resulting PU foam shell is slightly oversize (~3%) with respect to the size of the shell of the acetabular cup. The PU foam shell is subjected to LTAV deposition of titanium at 93° C. The side of the PU foam shell that will face the acetabular cup shell (ID side) is subjected to deposition for approximately 53 hours, whereas the deposition of titanium on the other side of the PU foam shell (OD side) is carried out for approximately 15 hours. The deposition is concluded when the thickness of the titanium coating reaches approximately 35 μm on the ID side and approximately 10 μm on the OD side of the PU foam shell. After the deposition is complete, the titanium-coated PU foam shell is attached to a blank of acetabular cup shell with the ID side of the PU foam shell facing the surface of the blank shell. The blank shell is made of titanium. The assembly of the blank titanium shell and the titanium-coated PU foam shell is placed in a retort equipped with an argon inlet and a thermometer. The retort and the assembly are placed into a furnace maintained at 1071-1121° C. under a continuous flow of argon at 40 ft$^3$/hour. After 5 to 10 minutes, the temperature in the retort reaches 550-600° C., indicating the complete burn-off of polyurethane. The retort is removed from the furnace and cooled to room temperature. The flow of argon through the retort is maintained during the cooling to minimize oxidation of the green foam. The resulting green foam on the surface of the shell has a pore size of approximately 980-1000 µm.

B. Pre-Sintering of the Green Foam.

To pre-sinter the green titanium foam, the shell is placed in a vacuum oven and the air is evacuated from the oven. Once the vacuum reaches $10^{-5}$ torr, the oven is heated to 427° C. at a ramp rate of approximately 8.3° C. per minute. The oven temperature is maintained at 427° C. for approximately 15 minutes. The heating is resumed at the same ramp rate until the temperature reaches 1316±22° C. The shell is maintained in the oven at 1316±22° C. for approximately 2 hours to complete the pre-sintering. The oven is cooled to room temperature, and the shell with the pre-sintered foam is removed.

C. Thickening of the Foam.

The pre-sintered titanium foam is sprayed with an ultra fine mist of a binder (2% aqueous solution of methyl cellulose, 25 cps, droplet size 30-40 µm). The stream of the binder is delivered by a Sonotek ultrasonic sprayer nozzle. After spraying, the binder is distributed throughout the foam. The binder-covered foam is then treated with titanium powder (Ti CP2, 40-80 µm particle diameter). The powder is sprayed by a metal powder sprayer onto and into the foam covered with methyl cellulose solution. The foam is air dried, and the shell with the foam is again pre-sintered as described above. After second pre-sintering, the cup is again treated with the binder solution, and another application of titanium powder is sprayed into the foam. The shell is then transferred to a vibratory table having a container filled with titanium powder (CP2, ~45 µm particle diameter). The vibratory table is turned on. The cup is immersed into the container until a rim of the shell is filled with the powder. The cup is removed from the container and placed on the vibratory table for 5 minutes. If the rim is not full after the vibrational treatment, the shell is again immersed into the titanium powder and the vibrational treatment is repeated for another 2 minutes. After the rim is full, the cup is air-dried for 12 hours at room temperature. The shell is ready for final sintering.

D. Final Sintering.

The shell is placed into a vacuum oven. Once the vacuum reaches $10^{-5}$ torr, the oven is heated at a ramp rate of 8.3° C. per minute to 427° C. The shell is kept at 427° C. for approximately 15 minutes. The heating is resumed at the same ramp rate until the temperature reaches 1316±22° C., and the shell is maintained at this temperature for approximately 2 hours. The oven temperature is raised to 1496±9° C. within 10 minutes. The shell is then maintained at this temperature for approximately 90 minutes to complete the sintering process. The shell is cooled to room temperature under vacuum, and then the oven is filled with inert gas. The pore size of the final foam is approximately 500-520 µm. The cup is machined to desired specifications.

EXAMPLE 2

The shell is processed as in the Example 1, but instead of the two powder treatments, the foam is thickened by vapor deposition (e.g., LTAVD, PVD, or CVD) of titanium until a 150-200 µm layer is deposited.

EXAMPLE 3

The shell is processed as in the Example 1, but the pore size of the polyurethane foam is 924 µm±89 µm, the pore size of the green foam after LTAV deposition is 967 µm±82 µm, and the pore size of the final foam is 614 µm±67 µm.

EXAMPLE 4

The shell is processed as in the Example 1, but only one powder treatment step is carried out, the pore size of the polyurethane foam (Crest, S-50 natural color) is 600 µm±50 µm, the pore size of the green foam after LTAV deposition is 630 µm±45 µm, and the pore size of the final foam is 480 µm±42 µm.

EXAMPLE 5

Protocol for Measuring Pore Sizes.

A sample of foam having a thickness of 1 to 2 mm is imaged by a Scanning Electron Microscope producing a field of view depicting approximately 5 mm×5 mm of the coated surface. Measurements are taken throughout ten distinct fields of view from a single sample. The distance between the web surfaces surrounding a pore is measured on all complete pores within a field of view. A complete pore is defined as one having all surrounding webs and pores intact. There are usually 2 to 4 complete pores within a single field of view, typically yielding an overall sample size of 20 to 40 readings. The mean and sample standard deviation are calculated and reported in microns.

Unless stated to the contrary, any use of the words such as "including," "containing," "comprising," "having" and the like, means "including without limitation" and shall not be construed to limit any general statement that it follows to the specific or similar items or matters immediately following it. Also, if a range is described in the specification and/or recited in the claims, the description/recitation of the range covers every data points within the range, as well as the beginning and ending points of the range. Each such data point, as well as the range defined thereby, should be considered as separately disclosed and/or claimed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of forming a porous scaffold for use in an implantable medical device, said method comprising:
 a) providing a polymer foam having a pre-determined thickness and webs defining a pore size ranging from about 500 µm to about 2000 µm;
 b) forming a skin of biocompatible metal on the webs of said polymer foam by low temperature arc vapor deposition LTAVD);
 c) heating said polymer foam and said metal skin above the decomposition temperature of said polymer foam in an inert gas atmosphere to decompose the polymer foam to form a porous metal network; and
 thickening webs of the porous metal network by applying a solution of a binder onto said webs, applying a biocompatible metal powder having a particle size of between 40 and 80 µm to the webs of the porous metal network, and sintering said metal powder covered metal network to form a porous coating on the webs to produce a porous scaffold wherein the webs define a pore size of 100 to 1000 µm.

2. The method of claim 1, wherein said thickening of said porous metal network is accomplished by applying the metal powder in a plurality of steps until said metal network has said pore size defined by the coated webs of 100 to 1000 μm.

3. The method of claim 1, wherein said pre-determined thickness of said polymer foam is between about 0.5 mm and about 10 mm.

4. The method of claim 3, wherein said pre-determined thickness of said polymer foam is between about 1 mm and about 5 mm.

5. The method of claim 3, wherein said pre-determined thickness is between about 1 mm and about 2 mm.

6. The method of claim 1, wherein said polymer foam is a polyurethane foam.

7. The method of claim 1, wherein said polymer foam has a pore size ranging from about 500 μm to about 2000 μm.

8. The method of claim 1, wherein said metal skin has thickness between about 1 μm and about 50 μm.

9. The method as set forth in claim 8 wherein, after the LTAVD step, the polymer foam webs have a first side and a second side with both sides having a metal skin.

10. The method of claim 9, wherein the thickness of said metal skin is about 35 μm on said first side and about 10 μm on said second side.

11. The method of claim 1, wherein said binder solution is an aqueous solution of methyl cellulose.

12. The method of claim 9, wherein after said heating of said metal webs the metal skin surrounds an empty core.

13. The method of claim 2, wherein said pre-determined pore size of said porous metal network is between about 300 μm and about 500 μm.

14. The method of claim 1, wherein said metal is selected from the group consisting of titanium, titanium alloy, cobalt chrome alloy, niobium and tantalum.

15. The method of claim 2, wherein the particle covered webs of the metal network include portions having a diameter of 20 to 100 microns.

16. A method of forming a porous scaffold for use in an implantable medical device, said method comprising:
   a) providing a polymer foam having a pre-determined thickness and webs defining a first pore size;
   b) forming a metal skin of biocompatible metal on said webs by low temperature arc vapor deposition of the metal;
   c) decomposing said polymer foam in an inert gas atmosphere thereby forming a porous metal network of metal webs;
   d) pre-sintering said porous metal network;
   e) contacting said pre-sintered metal webs with biocompatible metal particles in the presence of a binder, the particles having a size between 40 and 80 μm to form a porous coating on the webs;
   f) bonding said metallic particles to said pre-sintered metal webs to obtain a porous scaffold having pores defined by the particle coated webs defining a second pore size of between 100 and 1000 μm.

17. The method of claim 16, wherein said pre-determined thickness of said polymer foam is from about 0.5 mm to about 2 mm.

18. The method of claim 16, wherein said first pore size is from about 500 μm to about 2000 μm.

19. The method of claim 16, wherein said inert atmosphere is argon atmosphere.

20. The method of claim 16, wherein said second pore size is from about 100 μm to about 1000 μm.

21. The method of claim 16, wherein said metal particles and said pre-sintered porous metal network are bonded by sintering.

22. The method of claim 16, wherein the metal of said porous metal scaffold is selected from the group consisting of titanium, titanium alloy, cobalt chrome alloy, niobium and tantalum.

23. The method of claim 16, wherein the metal of said metal particles is selected from the group consisting of titanium, titanium alloy, cobalt chrome alloy, niobium and tantalum.

24. The method as set forth in claim 16 further comprising applying a biocompatible coating to the porous scaffold.

25. The method as set forth in claim 16 wherein the particle covered webs of the metal scaffold include portions having a diameter of 40 to 80 microns.

26. The method as set forth in claim 16 wherein after the decomposing of the polymer foam the metal skin network surrounds an empty core.

* * * * *